(12) United States Patent
Ginsberg et al.

(10) Patent No.: US 8,128,659 B2
(45) Date of Patent: Mar. 6, 2012

(54) SPINOUS PROCESS STABILIZATION DEVICE AND METHOD

(76) Inventors: Howard Joeseph Ginsberg, Toronto (CA); Devin Anand Singh, Mississauga (CA); Cari Marisa Whyne, Toronto (CA)

( * ) Notice: Subject to any disclaimer, the term of this patent is extended or adjusted under 35 U.S.C. 154(b) by 238 days.

(21) Appl. No.: 12/385,627

(22) Filed: Apr. 14, 2009

(65) Prior Publication Data
US 2009/0264927 A1    Oct. 22, 2009

Related U.S. Application Data

(60) Provisional application No. 61/071,137, filed on Apr. 14, 2008.

(51) Int. Cl.
*A61B 17/70* (2006.01)
(52) U.S. Cl. .................. 606/246; 606/248; 606/262
(58) Field of Classification Search .......... 606/246–249, 606/280–282, 286, 289–291, 300, 70, 71
See application file for complete search history.

(56) References Cited

U.S. PATENT DOCUMENTS
5,527,312 A    6/1996 Ray
(Continued)

FOREIGN PATENT DOCUMENTS
WO    2006/119235    5/2006

*Primary Examiner* — Eduardo C Robert
*Assistant Examiner* — Stuart S Bray
(74) *Attorney, Agent, or Firm* — Hill & Schumacher; Stephen W. Leonard; Lynn C. Schumacher

(57) ABSTRACT

A fixation device is provided to immobilize a spinal motion segment and promote posterior fusion, used as stand-alone instrumentation or as an adjunct to an anterior approach. The device functions as a multi-level fusion system including modular single-level implementations. At a single-level the implant includes a pair of plates spanning two adjacent vertebrae with embedding teeth on the medially oriented surfaces directed into the spinous processes or laminae. The complementary plates at a single-level are connected via a cross-post passed through the interspinous process gap The freedom of rotational motion of both the cross-post and collar enables the complementary plates to be connected at a range of angles in the axial and coronal planes accommodating varying morphologies of the posterior elements in the cervical, thoracic and lumbar spine. To achieve multi-level fusion the single-level implementation can be connected in series using an interlocking mechanism fixed by a set-screw.

56 Claims, 18 Drawing Sheets

U.S. PATENT DOCUMENTS

| | | |
|---|---|---|
| 5,667,506 A | 9/1997 | Sutterlin |
| 6,312,431 B1 | 11/2001 | Asfora |
| 6,364,883 B1 | 4/2002 | Santilli |
| 7,048,736 B2 | 5/2006 | Robinson |
| 2003/0040746 A1 | 2/2003 | Mitchell |
| 2003/0216736 A1* | 11/2003 | Robinson et al. ............... 606/61 |
| 2008/0183218 A1* | 7/2008 | Mueller et al. ................. 606/280 |
| 2009/0082813 A1* | 3/2009 | Long et al. .................... 606/282 |

* cited by examiner

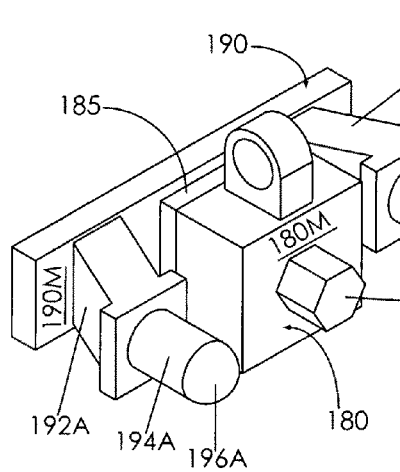
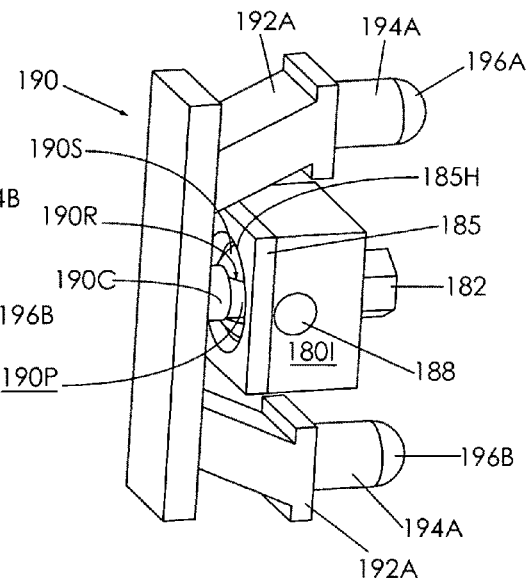
Fig. 17A　　　　　　　　Fig. 17B
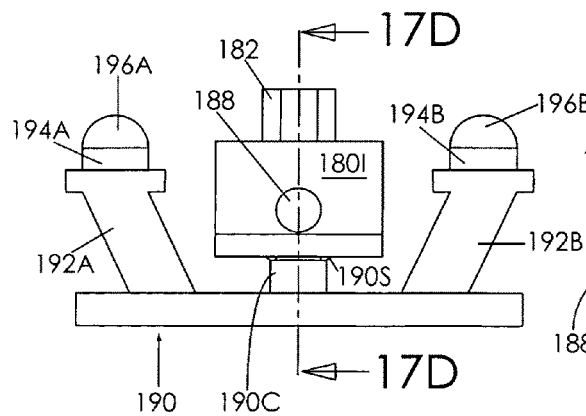
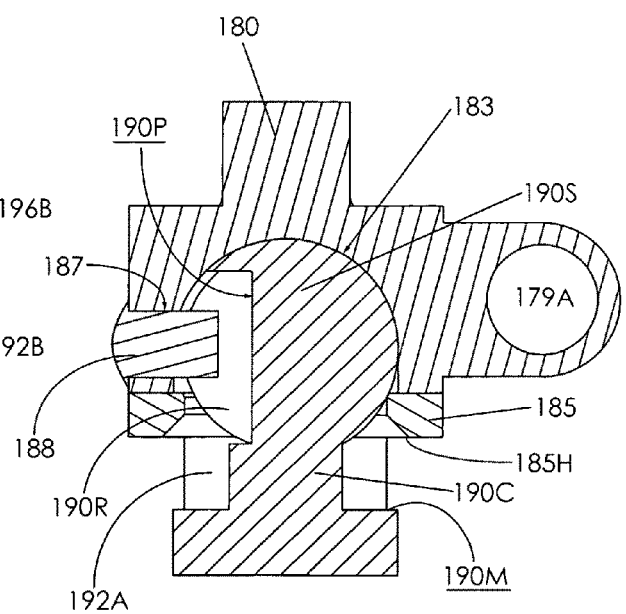
Fig. 17C　　　　　　　　Fig. 17D

SPINOUS PROCESS STABILIZATION DEVICE AND METHOD

CROSS REFERENCE TO RELATED APPLICATION

This patent application relates to, and claims the priority benefit from, U.S. Provisional Patent Application Ser. No. 61/071,137 filed on Apr. 14, 2008 entitled SPINOUS PROCESS STABILIZATION DEVICE AND METHOD and which is incorporated herein in its entirety.

FIELD OF THE INVENTION

The present invention generally relates to the field of medical devices, and, more particularly to a system for fusing the spinal column from the posterior aspect to restore stability. In the outlined embodiment, the system is comprised of a series of single level, dual-plate fusion devices which, utilizing the spinous processes and laminae of adjacent vertebral levels as the sole point of the bone-implant interface, immobilize a given spinal motion segment, thus promoting the bony fusion necessary to restore stability to a compromised spinal column.

BACKGROUND OF THE INVENTION

The functions of the spinal column are to provide stability and mobility, protect the spinal cord and control transmittance of the movement of the upper and lower extremities. Spinal stability is commonly defined as the ability of the spine, under physiological loads, to maintain its pattern of displacement so that there is no initial or additional neurological deficit, no major deformity, and no incapacitating pain [1]. Instabilities can arise due to many factors including trauma, degeneracy or metastasis which may result in pain, neurological deficit or even loss of mobility.

Several techniques requiring a wide range of device setups have been developed over the years to restore stability to a compromised spinal column. While the many techniques differ greatly in their implementation, they all serve the same purpose: spinal fusion. Spinal fusion is the process by which two or more vertebral levels are fused together with bone grafts and internal instrumentation to heal into a single, solid bone mass. The process eliminates motion between vertebral segments, which may be necessary to eliminate pain or re-stabilize the spine.

Currently, fusion is accomplished anteriorly, posteriorly or via a synergism of the two. The major anterior approach for fusion is an interbody fusion in which a device having variable height is inserted in the disc space between adjacent vertebral levels to replace part or all of a damaged disc or to restore geometry to a collapsed vertebral body. The interbody device comprises a hollow cylinder in which bone graft is packed to promote fusion of the adjacent levels and osseointegration of the implant. In many cases, the native forces experienced in the spine will require a supplemental posterior fusion or stabilization to re-enforce the anterior instrumentation.

Currently, posterior fusion is predominated by pedicle screw-rod systems. Pedicle screw fixation was first described in North America by Harrington and Tullos in 1969 but did not gain full acceptance until the early part of the 1980s. In transpedicular screw fixation, screws are passed in an anteromedial direction through the pedicles of a vertebra and into the body centrum of the same vertebra. One of two screw trajectories can be used: the anatomical or the straight-forward approach. The anatomical approach, used by the majority of surgeons today, provides the largest possible bone channel for the placement of the screw, but requires the use of poly-axial screws which are locked in place and joined together through rod or plate linkages.

Installation of pedicle screws is heavily dependent on surgical expertise. The angle of insertion into the pedicle is paramount to complication avoidance and even minor misalignments can lead to insult of the vertebral artery in the cervical region if the placement is too lateral. Implications of medial violation of the pedicle can be severe neurological deficit in any region of the vertebral column. The alignment of these screws is a difficult task due to the variability present in the transverse pedicle width throughout the vertebral column. This range of pedicle widths dictates the angle of insertion of the screw.

The expanding knowledge of spinal column biomechanics and the refinements in material selection has slowly shifted the dangers associated with spinal instrumentation from device failures to surgical proficiency. As seen with pedicle screw-rod systems, the dangers encountered are predominantly related to the anatomy of the posterior spine, as described above. Improper insertion of the pedicle screws can lead to insult to the vertebral artery or intrusion into the spinal canal, leading to severe neurological deficit. Due to the risks associated with the procedure, extreme caution is necessary for proper installation. This has led to large surgical exposure for extended periods of time which, in turn, results in increased patient blood loss intraoperatively and longer duration recovery times.

Alternative posterior techniques have been attempted in the past which address some of the inherent risks associated with the pedicle screw-rod systems. In these techniques, adjacent spinous processes are wired together via holes created in the spinous processes. In the case of the Roger's approach the wires are used independently as the method of fixation while the Bohlman's and Dewar procedures incorporate bone graft to supplement the wiring. These techniques have all fallen out of favour owing to their inability to provide sufficient motion restriction for bony fusion formation. Moreover, these techniques are capable of resisting flexion (tension) but not extension (compression) since they rely on wires to hold the vertebrae together. Even with the addition of a bone graft supplement, the insecure fitting of the graft permits levels of motion detrimental to the fusion process.

It is possible to accomplish a posterior spinal fusion through the use of plating systems which contact the vertebrae via the spinous processes. The use of plates allows for motion restriction in both flexion and extension, thus enabling the necessary constraint needed for a healthy bone fusion to occur. In general, these plating systems will comprise of a pair of plates placed on each lateral side of the spine and connected via cross-posts. The plates may be found in various sizes and shapes to accommodate the large diversity of spine morphologies found in the general population.

U.S. Patent Publication No. 2003/0040746 issued to Mitchell, Landry et al. discloses a system which incorporates two plates positioned on contralateral sides of the spinous processes and coupled together with bolts passed through holes, which were pre-drilled in the cortical bone of the superior and inferior spinous processes involved in the fusion. Although this device begins to address the risks involved in the pedicle screw-rod systems and accomplishes both tensile and compressive force restriction in the spinal column, the mode of implementation does not allow fusion of a larger motion segment, nor does it accommodate the natural kyphotic or lordotic curvature over the restricted motion segment. Moreover, the method of connection of complementary plates requires compromise of the structural integrity of the spinous processes, the very element used for the bone-implant interface.

U.S. Pat. No. 5,527,312 issued to Ray, which is incorporated by reference as if fully set forth herein, describes a system incorporating a facet screw anchor and fixation bar for immobilizing two vertebrae relative to each other. A portion of a fixation bar is wrapped around a portion of a superior vertebra pedicle. The fixation bar is secured to a facet screw anchor and the facet screw anchor is positioned through a facet joint of the superior vertebra and into the base of a transverse process of an inferior vertebra. The fixation bar and facet screw immobilize the superior vertebra and the inferior vertebra.

SUMMARY OF THE INVENTION

The present invention provides a device for stabilizing a portion of a spinal column which works by joining together adjacent spinous processes to stabilize a portion of a spine.

An embodiment of the present invention provides a device for stabilizing a portion of a human spine, comprising:

a first pair of longitudinal plates, wherein a medial surface of each plate of said first pair of longitudinal plates is adapted to contact two adjacent spinous processes when said first pair of longitudinal plates are arranged on contralateral sides of a sagittal plane;

a post adapted to connect said first pair of longitudinal plates within an interspinous gap between said two adjacent spinous processes; and a plate connection means on each plate of said first pair of longitudinal plates for optionally connecting said first pair of longitudinal plates to an additional pair of longitudinal plates;

wherein each plate of said additional pair of longitudinal plates is adapted to contact an additional adjacent spinous process when said additional pair of longitudinal plates is connected to said first pair of longitudinal plates and when said additional pair of longitudinal plates is arranged on contralateral sides of said sagittal plane; and wherein said connection means accommodates a kyphotic or lordotic curvature of said spine.

More particularly, an embodiment of the present invention provides a fixation device to immobilize a spinal motion segment and promote posterior fusion, used as stand-alone instrumentation or as an adjunct to an anterior approach. The device functions as a multi-level fusion system compromised of modular single-level implementations. At a single-level the implant includes a pair of plates spanning two adjacent vertebrae with embedding teeth on the medially oriented surfaces directed into the spinous processes or laminae. The complementary plates at a single-level are connected via a cross-post with a hemispherical base and cylindrical shaft passed through the interspinous process gap and ratcheted into an expandable collar. The expandable collar's spherical profile contained within the opposing plate allows for the ratcheting mechanism to be correctly engaged creating a unidirectional lock securing the implant to the spine when a medially directed force is applied to both complementary plates using a specially designed compression tool. The freedom of rotational motion of both the cross-post and collar enables the complementary plates to be connected at a range of angles in the axial and coronal planes accommodating varying morphologies of the posterior elements in the cervical, thoracic and lumbar spine. To achieve multi-level fusion the single-level implementation can be connected in series using an interlocking mechanism fixed by a set-screw. The interlock design allows accommodation of native spinal curvature in the sagittal plane. The device provided in a range of plate and cross-post sizes establishes a fully expandable fusion system capable of incorporating adjacent superior and inferior levels at the time of initial installation or at any later time should degradation of adjacent levels occur.

The present invention also provides a compression tool for installing a pair of longitudinal plates to stabilize a spine, said pair of longitudinal plates including a first plate and a second plate, each plate including a lateral surface and a medial surface whereby said medial surfaces face each other when said plates are contacted with said two adjacent spinous processes or laminae, wherein said plates are adapted to be connected by a post within an interspinous gap between said two adjacent spinous processes, wherein a proximal end of said post is slidably received through a first aperture in said first plate, said first aperture extending from said lateral surface of said first plate to said medial surface of said first plate, wherein said second plate houses a collar in a second aperture in said second plate, wherein said collar is adapted to connect to a distal end of said post when a compressive force is applied along an axis of said collar, wherein said post and said first aperture are adapted to permit limited polyaxial orientation of said post when said post is received within said first aperture and wherein said collar and said second aperture are adapted to permit limited polyaxial orientation of said collar when said collar is housed within said second aperture, wherein said compression tool comprises:

first and second handles pinned at a first pin located on a principal axis;

first and second leverage arms pinned at a second pin located inferior to said first pin on said principal axis, wherein said first leverage arm is pinned to said first handle at a third pin located between said first and second pins at a first lateral distance from said principal axis, and said second leverage arm is pinned to said second handle at a fourth pin located between said first and second pins at a lateral distance from said principal axis equal to said first distance on an opposite side of said principal axis, wherein said third and fourth pins lie in a line orthogonal to said primary axis;

first and second contact pieces pinned to a distal end of said first and second leverage arms, wherein said first and second contact pieces each include a medial surface, and wherein said medial surfaces are oriented inwardly towards said primary axis, said medial surface of said first contact piece including a means for contacting a lateral surface of said post at a proximal end of said post when said post is received within said first aperture, and said medial surface of said second contact piece including a means for contacting a lateral surface of said collar when said collar is housed within said second aperture;

a first platform located on a lateral side of said first contact piece, said platform connected to said first contact piece by a first polyaxial arm, wherein said first platform contains a medial surface, and further includes two posts projecting from said medial surface, and wherein said two posts are arranged on opposite sides of said contact piece within a plane containing said means for contacting a lateral surface of said post, and a distal end of each said post is adapted to contact a point located on a lateral surface of said first plate when said means for contacting a lateral surface of said post is contacted with said post;

a second platform located on a lateral side of said second contact piece, said platform connected to said second contact piece by a second polyaxial arm, wherein said second platform contains a medial surface, and further includes two posts projecting from said medial surface, and wherein said two posts are arranged on opposite sides of said contact piece within a plane containing said means for contacting said collar, and a distal end of each said post is adapted to contact a point located on a lateral surface of said second plate when said means for contacting a lateral surface of said collar is contacted with said collar;

whereby actuation of said tool causes a medially directed compressive force to be applied to said post and collar, thereby connecting said post and collar, while permitting limited polyaxial orientation of said first and second plates, thus enabling said first and second plates to be oriented in various angles.

The invention additionally provides a method for stabilizing a portion of a spine, comprising the steps of:

contacting a medial surface of each plate of a first pair of longitudinal plates with two adjacent spinous processes or laminae, thereby arranging said first pair of longitudinal plates on contralateral sides of a sagittal plane;

connecting said first pair of longitudinal plates within an interspinous gap between said two adjacent spinous processes with a post; and serially connecting one or more additional pairs of longitudinal plates to said first pair of longitudinal plates with a plate connection means, contacting a medial surface of each plate of each pair of said additional pairs of plates with a spinous process at a first distal end of each plate of said one or more additional pairs of plates, and connecting each plate within a pair of said one or more additional pairs of longitudinal plates within an interspinous gap with a post;

wherein:

said plate connection means is included on one or both distal ends of said first pair of plates and a second distal end of each plate in said one or more additional pairs of plates;

said plate connection means accommodates a kyphotic or lordotic curvature of said spine; and said serial connection of said one or more additional pairs of longitudinal plates allows for connecting adjacent pairs of plates along a continuous arc, yielding a device that can accommodate a various geometries and morphologies of a posterior vertebral arch of said spine at different vertebral levels.

A further understanding of the functional and advantageous aspects of the invention can be realized by reference to the following detailed description and drawings.

BRIEF DESCRIPTION OF THE DRAWINGS

Embodiments of the present invention are described in greater detail with reference to the accompanying drawings in which:

FIGS. 17A, 17B, 17C and 17D show detailed views of a first contact piece with a polyaxial arm that supports an interlocking plate during compression.

DETAILED DESCRIPTION OF THE INVENTION

Generally speaking, the systems described herein are directed to a device and system for stabilizing a portion of a spinal column which joins together adjacent spinous processes to stabilize a portion of a spine. As required, embodiments of the present invention are disclosed herein. However, the disclosed embodiments are merely exemplary, and it should be understood that the invention may be embodied in many various and alternative forms.

The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to a spinal column which joins together adjacent spinous processes to stabilize a portion of a spine.

As used herein, the term "about", and "approximately" when used in conjunction with ranges of dimensions, temperatures or other chemical or physical properties or characteristics is meant to cover slight variations that may exist in the upper and lower limits of the ranges so as to not exclude embodiments where on average most of the dimensions, temperatures, or any other chemical or physical properties or characteristics are satisfied but where statistically they may exist outside this range.

Figure 1:
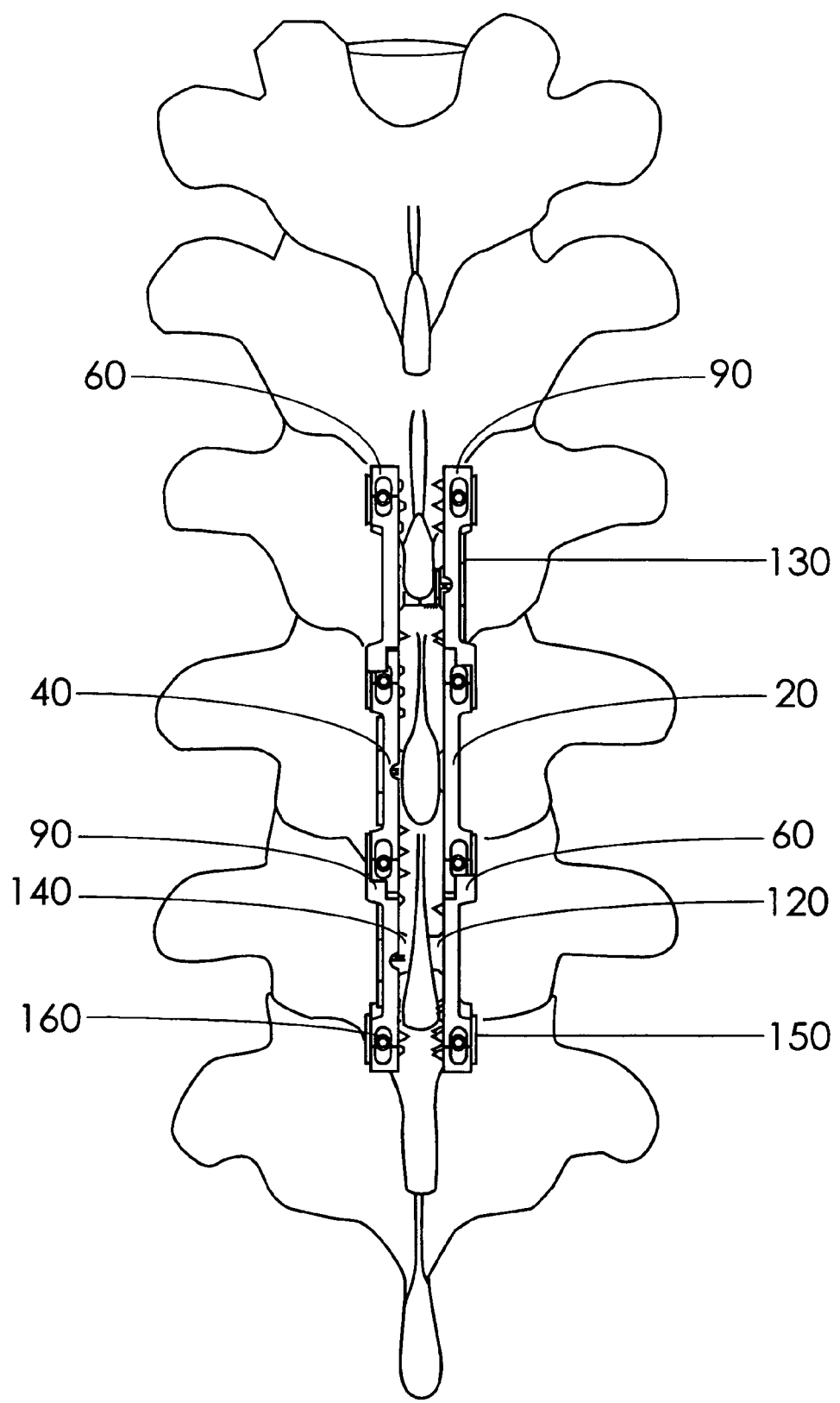
FIG. 1 shows a posterior view of a portion of the spine with the device of the present invention fixed on the thoracic spine to provide a three-level fusion.
Figure 2:
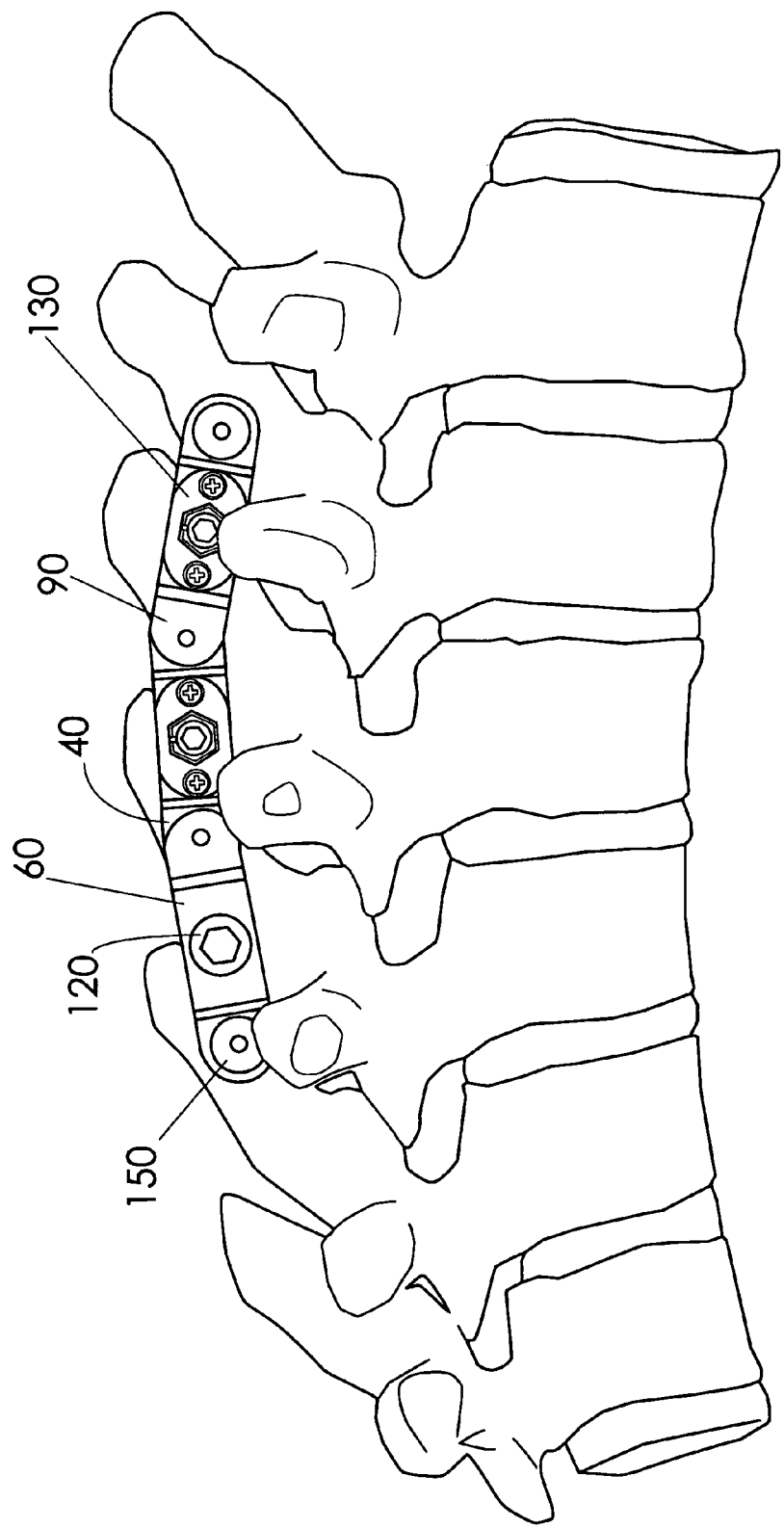
FIG. 2 shows a lateral view of the instrumentation of FIG. 1.

Referring to FIG. 1, a posterior view of a portion of the spine with the device of the present invention fixed on the thoracic spine to provide a three-level fusion while FIG. 2 shows a lateral view of the instrumentation of FIG. 1.

Figure 3:
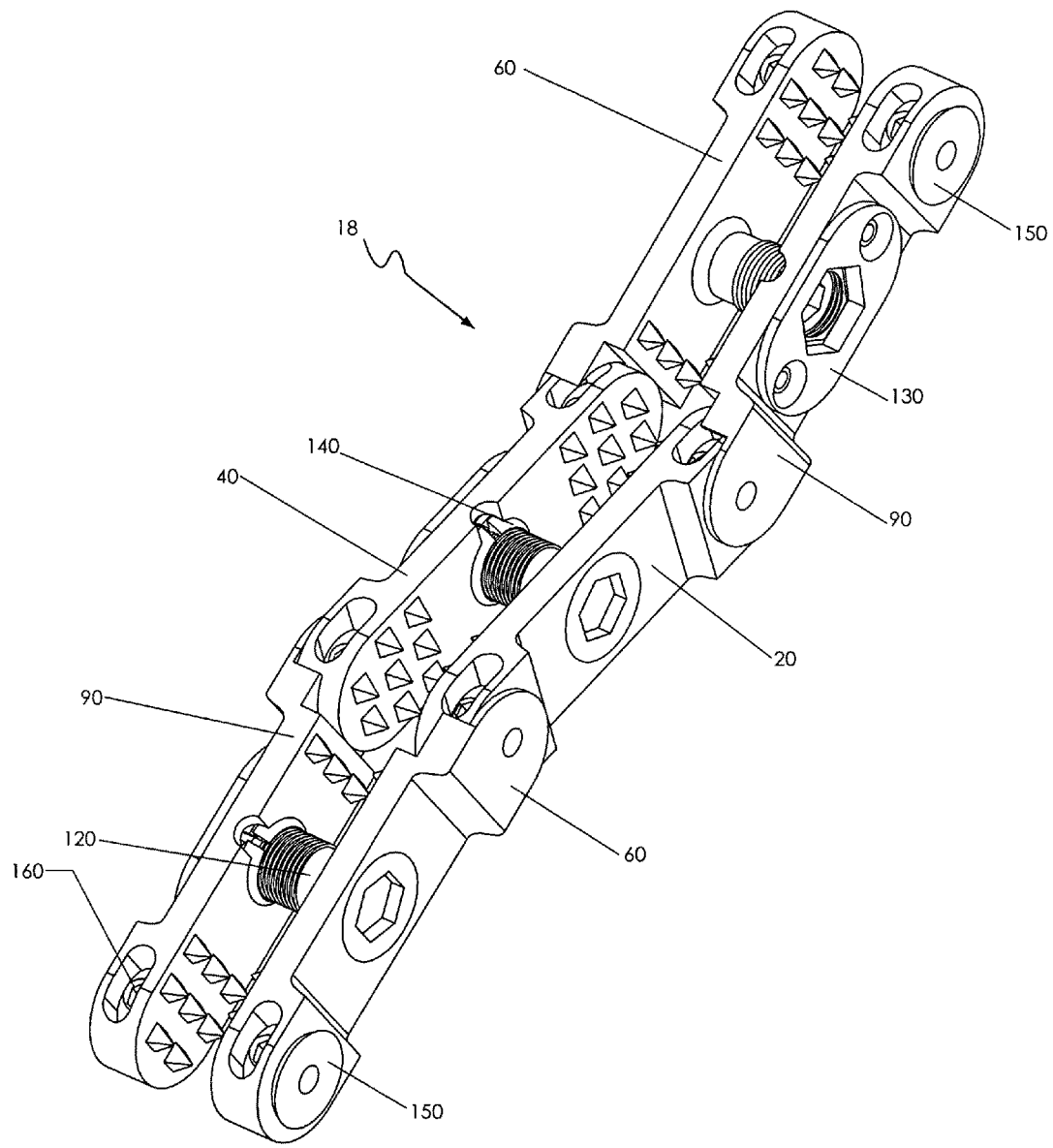
FIG. 3 shows a perspective view of the spinal stabilization device of the present invention.
Figure 4:
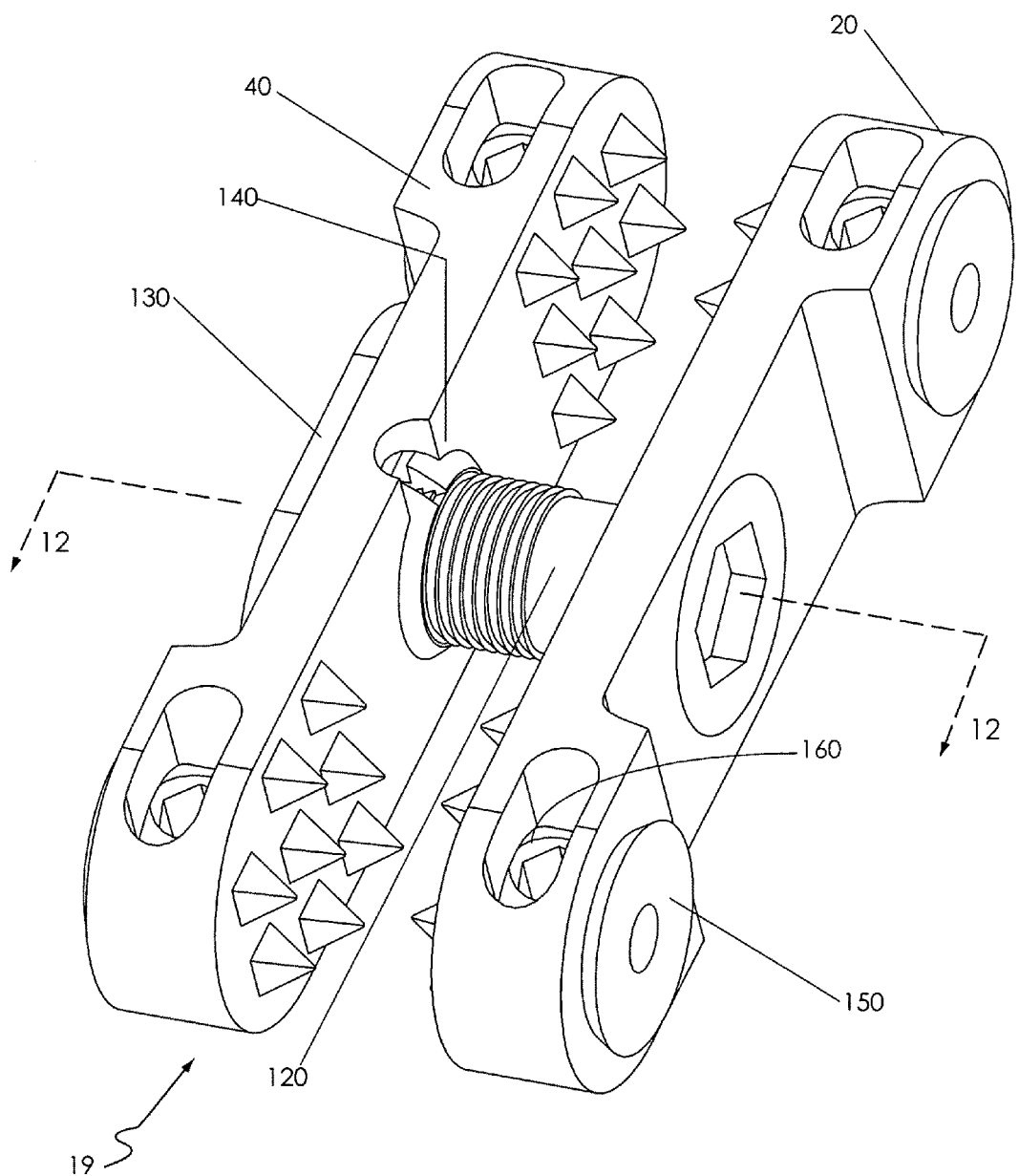
FIG. 4 shows a perspective view of the spinal stabilization device at a single level capable of extension in both the superior and inferior direction to provide the desired multi-level fusion.
Figure 5A:
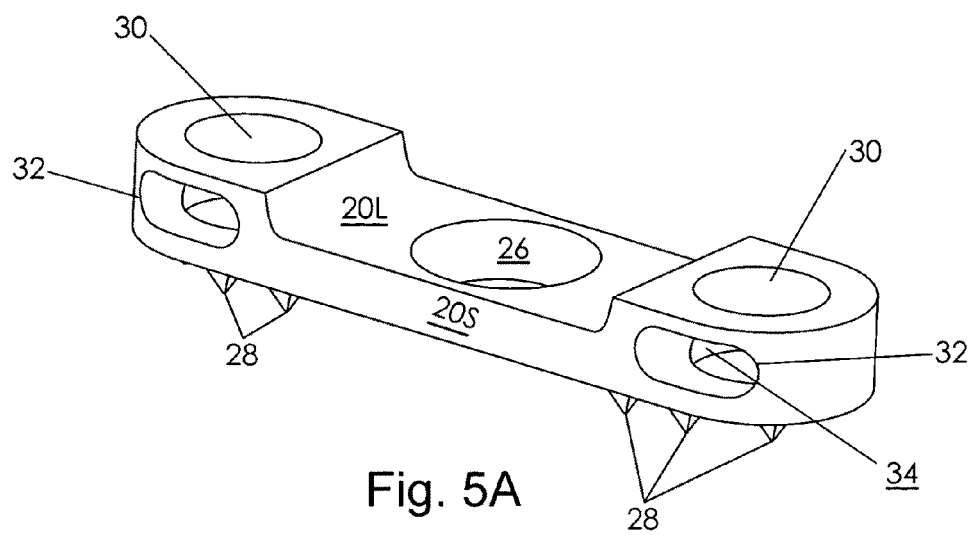
FIGS. 5A, 5B and 5C shows detailed views of the cross-post plate of the initial single-level installation.
Figure 5B:
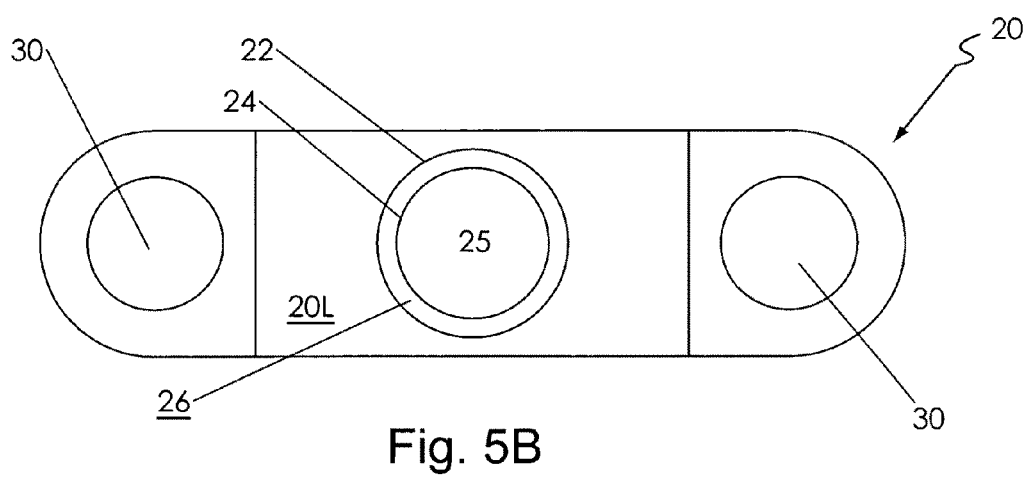
Figure 5C:
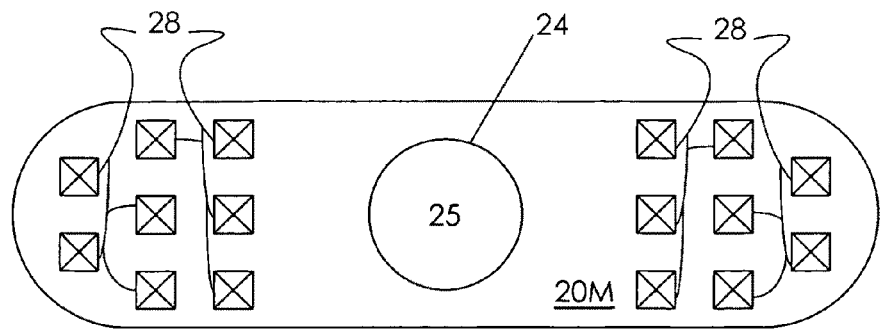
Figure 6A:
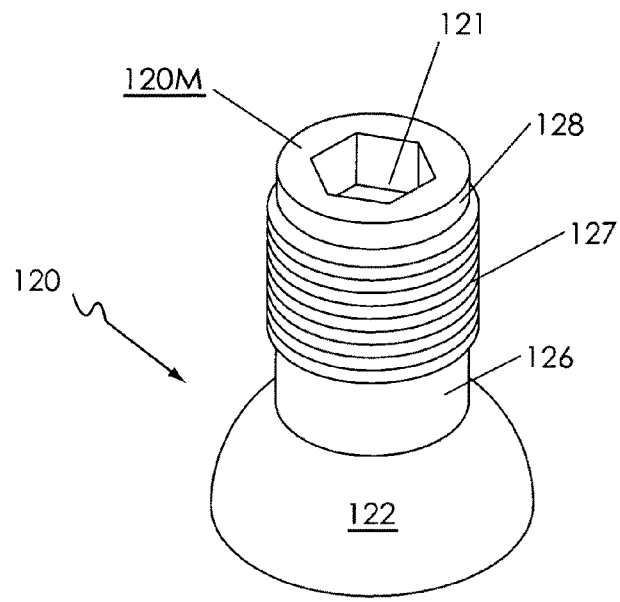
FIGS. 6A, 6B, 6C shows detailed views of the cross-post, one half of the uni-directional locking mechanism used to connect complementary plates of the system via the interspinous process gap.
Figure 6B:
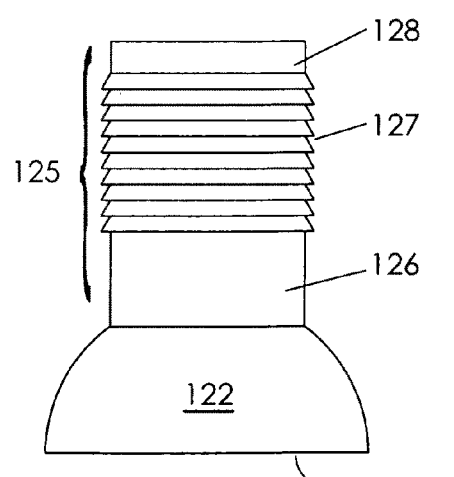
Figure 6C:
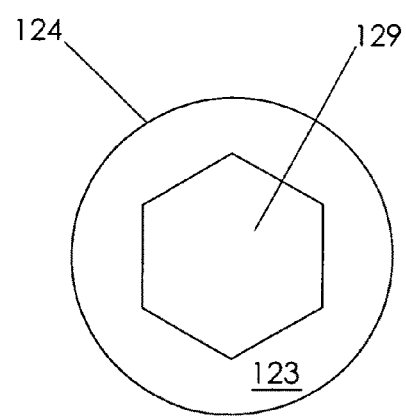
Figure 7A:
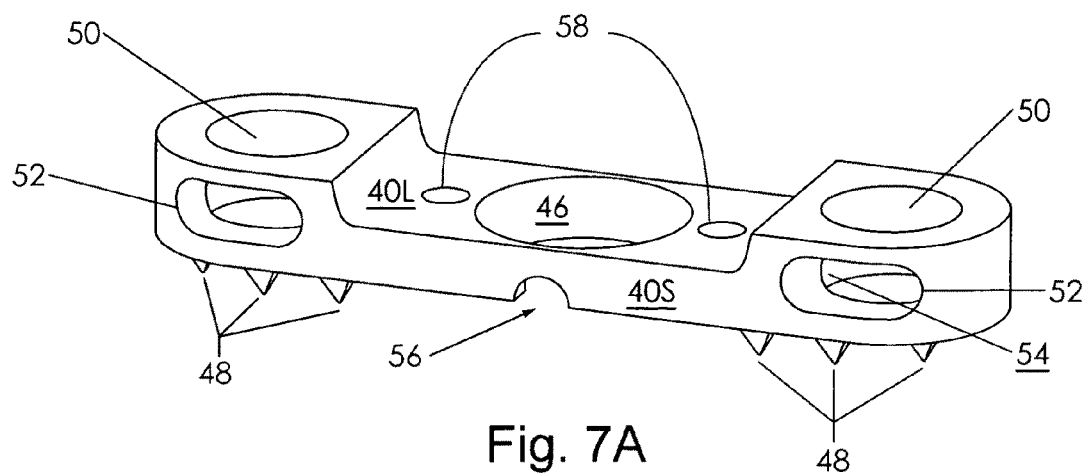
FIGS. 7A, 7B and 7C shows detailed views of the locking plate of the initial single-level installation.
Figure 7B:
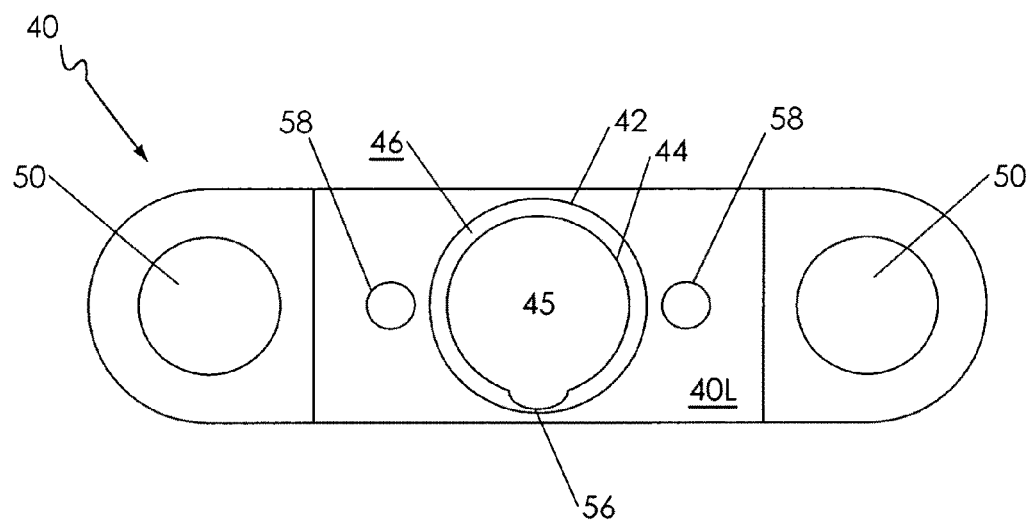
Figure 7C:
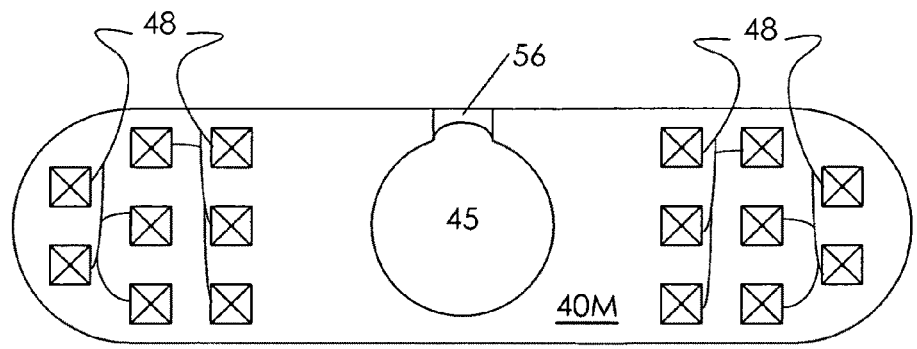
Figure 8A:
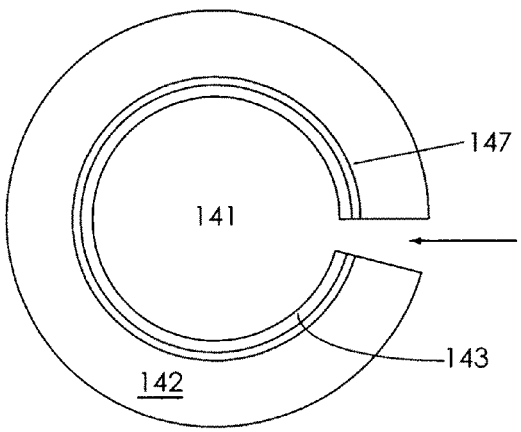
FIGS. 8A, 8B, 8C, 8D and 8E shows detailed views of the expandable collar located within the confines of the locking plates, the collar represents the second half of the unidirectional lock complimented by the cross-post of FIGS. 6A and 6B.
Figure 8B:
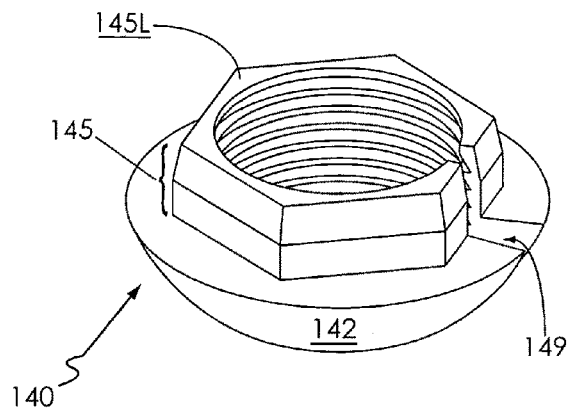
Figure 8C:
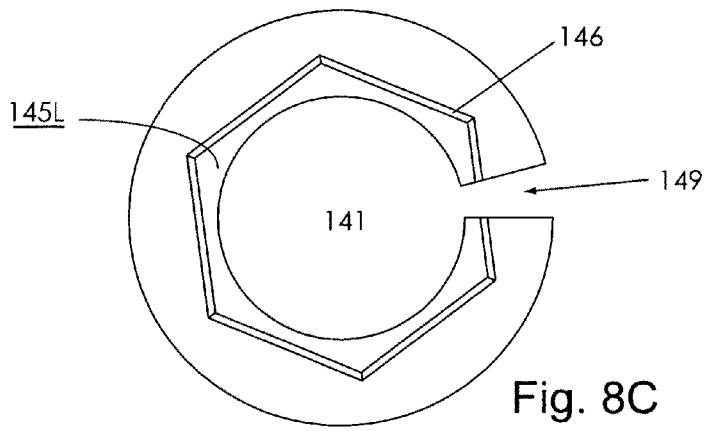
Figure 8D:
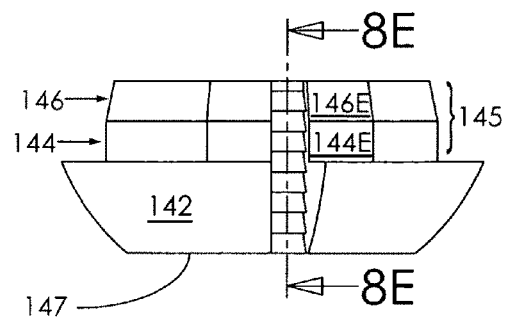
Figure 8E:
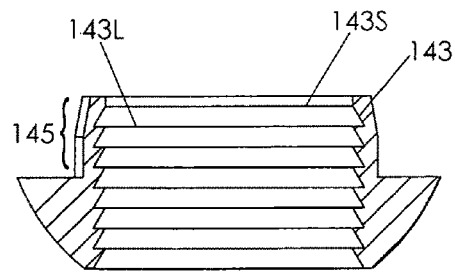
Figure 9A:
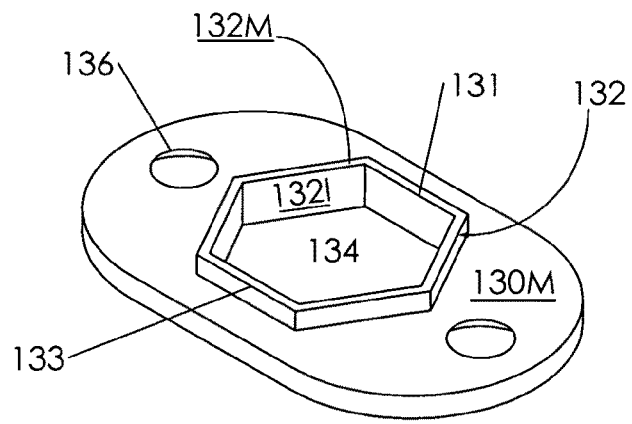
FIGS. 9A, 9B and 9C show detailed views of a restriction washer forming part of the present invention.
Figure 9B:
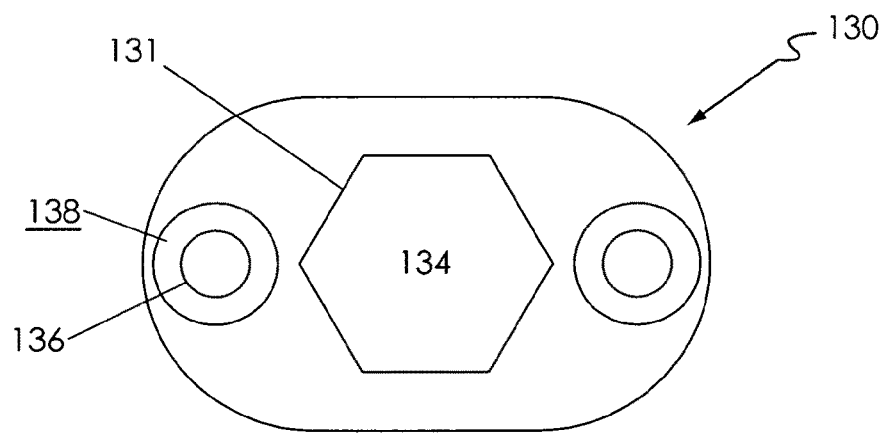
Figure 9C:
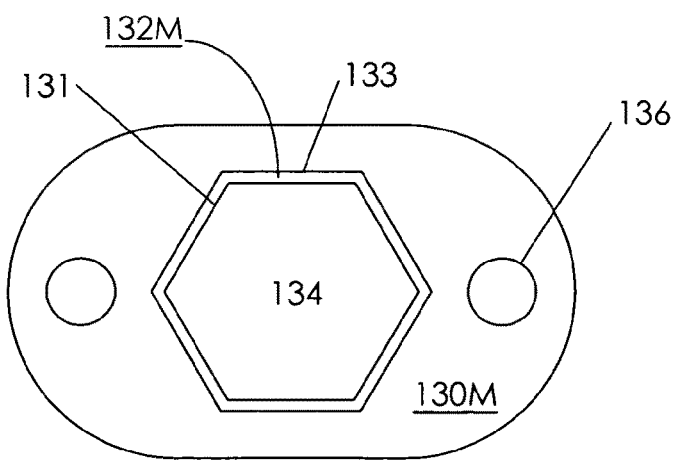
Figures 10A, 10B:
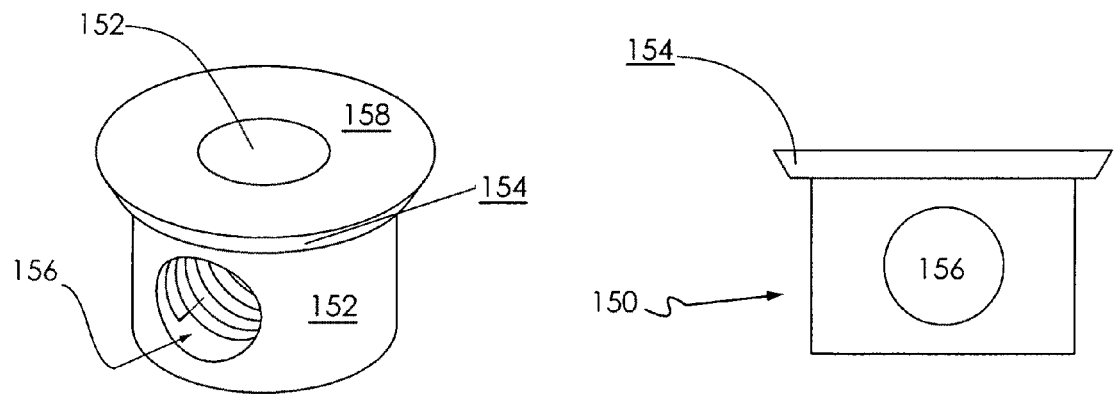
FIGS. 10A and 10B show detailed views of a stopper forming part of the present invention.
Figures 11A, 11B:
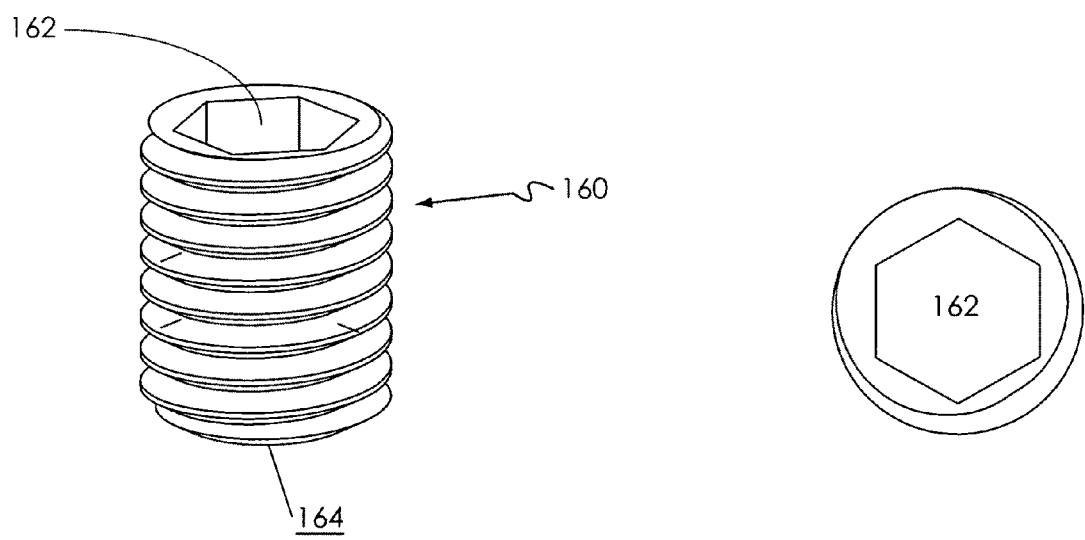
FIGS. 11A and 11B show detailed views of a set screw used to engage the interlocking mechanism of the present device.

Referring to the drawings in detail, utilizing FIGS. 3 and 4 as a representation of the entire construct, the device 18 according to the current illustrated embodiment is a multi-level posterior spinal fusion device which clamps the spinous processes and/or laminae at any level of the spine. The device 18 is designed to allow multilevel fusion at the time of insertion as well as permit expansion from single or multilevel constructs to fuse additional levels at any later time. During installation of the device the central level of the desired, restricted motion segment must be implemented with device 19 which has the capability of expanding in both the superior and inferior directions.

At a single level the device 19 comprises a cross-post plate 20, locking plate 40, a cross-post 120, a restriction washer 130 and an expandable collar 140. The cross-post 120 serves to connect the cross-post plate 20 via the interspinous process gap to its complementary locking plate 40 located on the contralateral side of the spine. The proximal end of the cross-post 120 is seated in the cross-post plate 20. At the distal end, the cross-post 120 has ratcheted teeth 127 which are accepted into socket 141 of the expandable collar 140 creating a unidirectional locking mechanism. The expandable collar 140 is located within the locking plate 40 and is held in place by the restriction washer 130. When the ratcheted teeth 127 are engaged with the opposing ratchet 143 located within slot 141 of the expandable collar 140 the two contralateral plates clamp the spinous processes and/or lamina of the posterior vertebral elements.

On the medial surfaces 20M and 40M of the cross-post plate 20 and the locking plate 40 respectively there are square based pyramidal teeth 28 and 48. When the plates have been clamped to the posterior elements the teeth embed themselves into the strong cortical bone of the posterior elements serving to anchor the position of the device with respect to the longitudinal axis of the spine. This is an overview of the basic assembly of the device 19 at a single level.

Referring to FIGS. 5A, 5B, 5C and 6A and 6B, the hemispherical base 122 of the cross-post 120 is in contact with the hemispherical surface 26 of the cross-post plate with the shaft 125 passing through socket 25 of the same plate. The maximum diameter 22 of socket 25 is equal in diameter to the maximum diameter 124 of the hemispherical base 122 of cross-post 120 allowing both hemispherical features to have the same radius of curvature as they progress from the lateral surface 20L to the medial surface 20M of the cross-post plate 20.

The minimum diameter 24 of the socket 25 is larger than the combined diameter of the shaft 125 and ratcheted teeth 127 of the cross-post 120. This difference in diameter allows the shaft 125 to pass through socket 25 at which point the contact between the hemispherical base 122 and the hemispherical surface 26 allows the cross-post 120 to move freely about all three axes creating a poly-axial connection between the cross-post plate 20 and the locking plate 40. The difference between the minimum diameter 24 of socket 25 and the minimum diameter of the proximal portion 126 of shaft 125 once it has passed through socket 25 allows for a conical range of motion of up to 20° before interference between the cross-post 120 and the medial surface 20M of the cross-post plate 20 restricts any further motion.

The end result of combining the cross-post 120 with the cross-post plate 20 is the ability of the medial surface 20M of the cross-post plate to make contact with the surface of the spinous processes and/or laminae at varying angles in the axial and coronal plane. This permits the principle axis of the embedding teeth 28 to be oriented perpendicular to the surface of the posterior elements assuring strong anchoring of the embedding teeth 28 into the cortical bone. Additionally, this ensures that the cross-post 120 lies perpendicular to the longitudinal axis of spine completely within the interspinous process gap.

In one embodiment, the cross post may be received within an aperture in said locking plate and locked by a set screw within said locking plate. In an alternative embodiment, said locking plate houses a nut, and said nut is threaded onto distal end of said cross-post to lock the plates. The nut housing may be adapted to limit a rotation of said nut. In a preferred embodiment, said cross-post is received in an expandable collar housed in said locking plate, as described below.

Making reference to FIGS. 6A, 6B, 7A, 7B, 7C, 8A to 8E, and 9A, 9B and 9C, the shaft 125 of the cross-post 120 is received at its distal end into socket 141 of the expandable collar 140. The expandable collar 140 is housed within in the locking plate 40 and is held in position by the restriction washer 130. The expandable collar 140 is composed of a spherically curved base 142 and a hexagonal upper half 145. The spherically curved base 142 of the expandable collar 140 is in contact with the hemi-spherical surface 46 of the locking plate 40. Similar to the cross-post 120 and cross-post plate 20, the maximum diameter 42 of the socket 45 is equal in diameter to the sphere from which the expandable collar 140 is derived allowing both spherical features to interact smoothly along identical radii of curvature. The minimum diameter 44 of the socket 45 is larger than minimum diameter 147 of the expandable collar 140.

This difference in minimum diameters allows the expandable collar 140 to extend past the medial surface 40M of the locking plate 40 into the interspinous process gap where it contacts the shaft 125 of the cross-post 120. The distal end of the shaft 125 is received into socket 141 of the expandable collar 140. Within socket 141 of the expandable collar 140 contains the complementary ratchet 143 to the ratcheted teeth 127 found on the shaft 125 of the cross-post 120. In order for the shaft 125 with ratcheted teeth 127 to pass through socket 141 the expandable collar has a segment removed creating slot 149 which allows the collar 140 to expand and return to its neutral position as the ratcheted teeth 127 of the shaft 120 interact with the complementary ratchet 143 within socket 141 of the expandable collar 140. In a preferred embodiment, the angular with of said segment is approximately 15°.

For the ratchet mechanism to correctly engage, the shaft 125 needs to enter the socket 141 such that the diameter of the ratcheted teeth 127 is concentric to the major diameter 143L of socket 141. Since the cross-post 120 is capable of poly-axial motion the expandable collar 140 must to also allow poly-axial motion to ensure the acceptance of shaft 125 into socket 141 at the correct angle. The contact of the spherical surface 46 of the locking plate 40 with the spherical surface 142 of the expandable collar 140 allows the collar 140 to move in three axes similar to the cross-post 120 ensuring the ratcheting mechanism can be correctly engaged.

Figure 12:
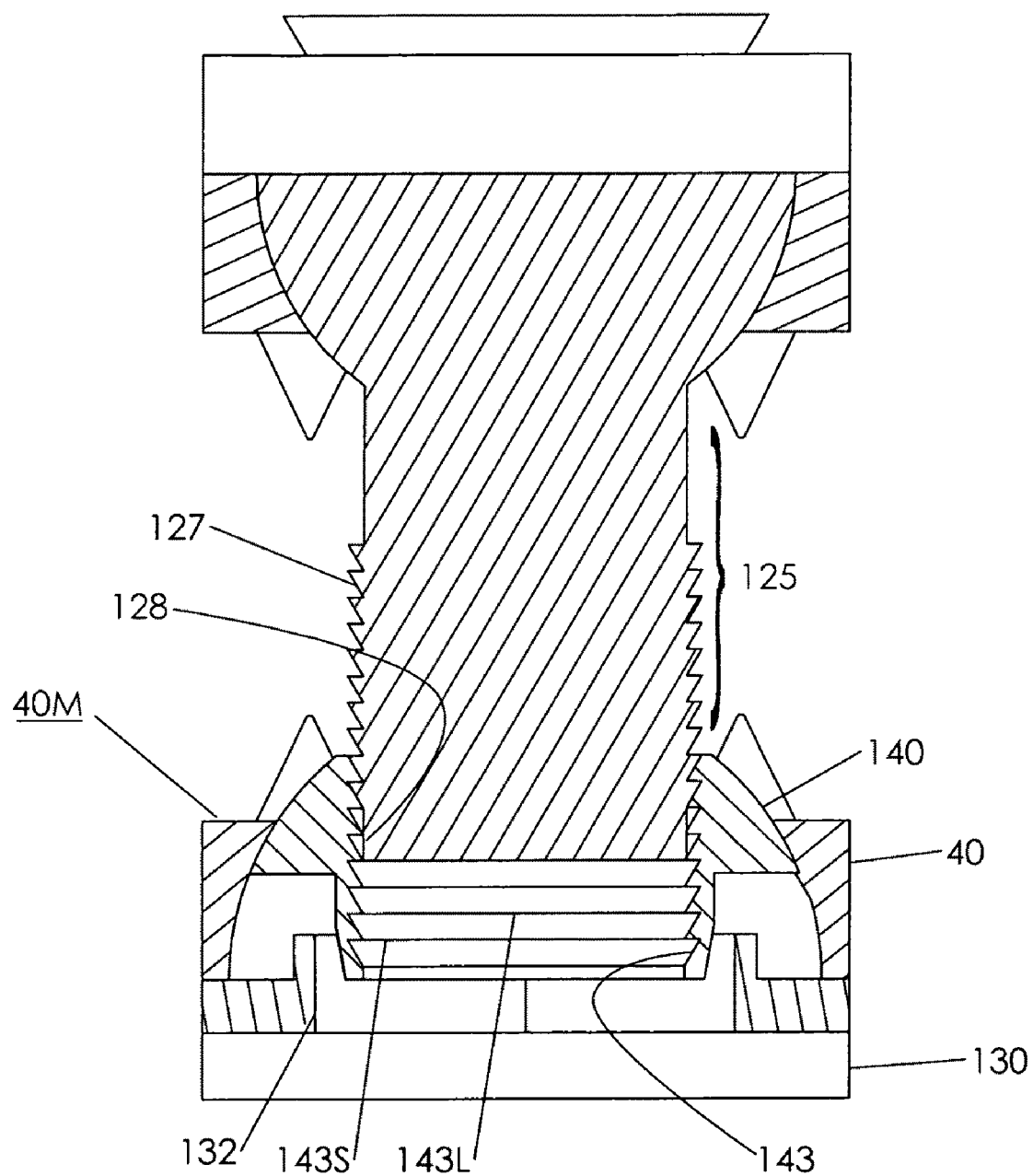
FIG. 12 is a section taken through the assembly of FIG. 4 on the axis of the cross-post and viewed in a plane containing the axis of the cross-post and perpendicular to the posterior surfaces of the plates and viewed in the direction of the arrows 12-12.
Figure 13A:
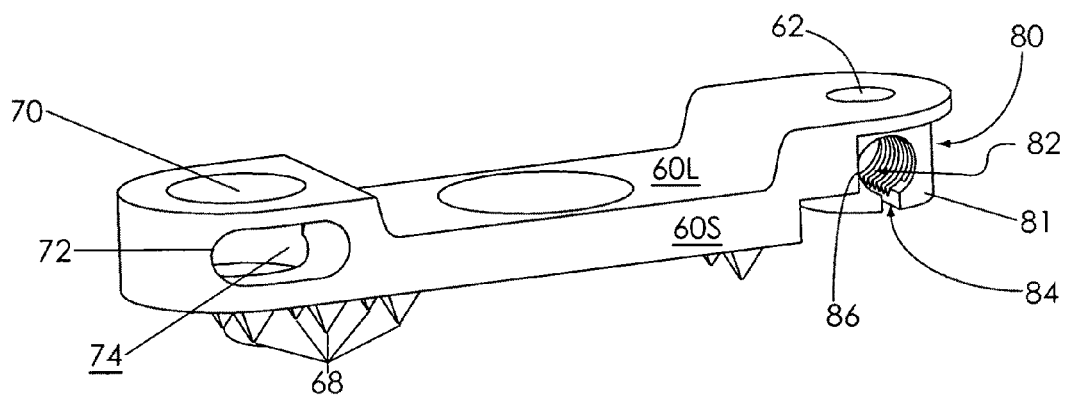
FIGS. 13A, 13B, 13C and 13D show detailed views of an extension cross-post plate and the male and female portions of the interlocking mechanism.
Figure 13B:
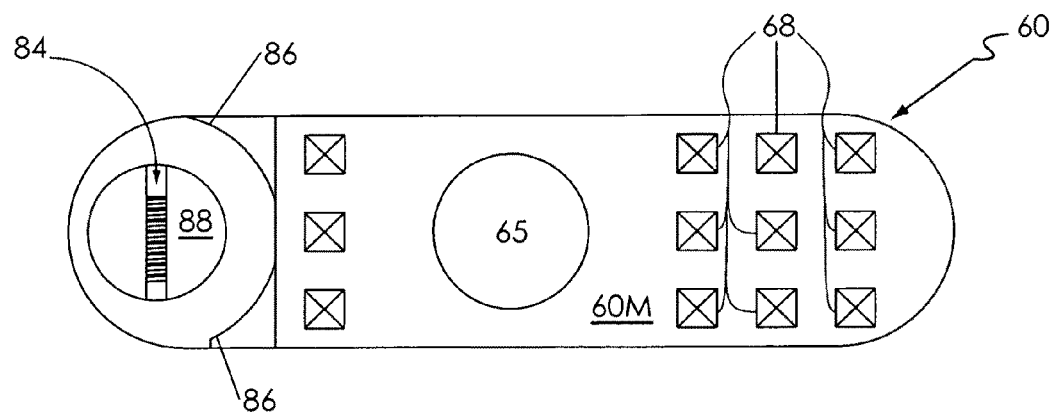
Figure 13C:
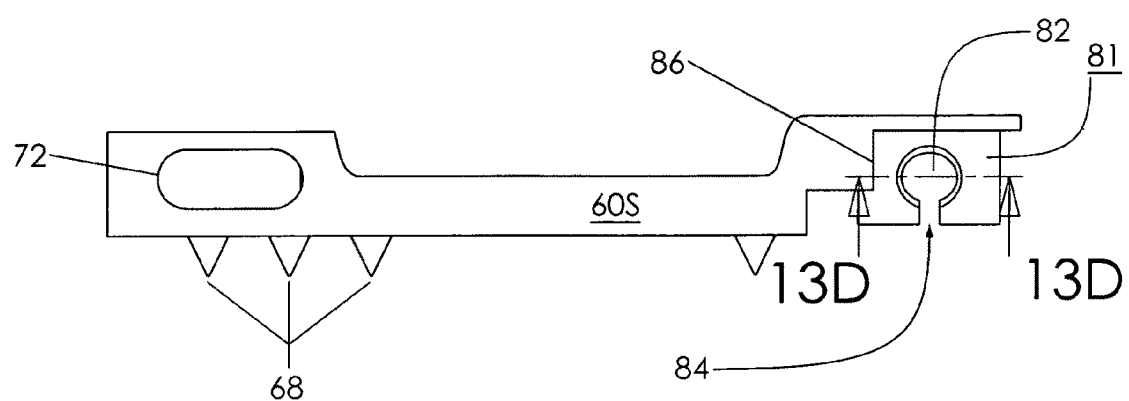
Figure 13D:
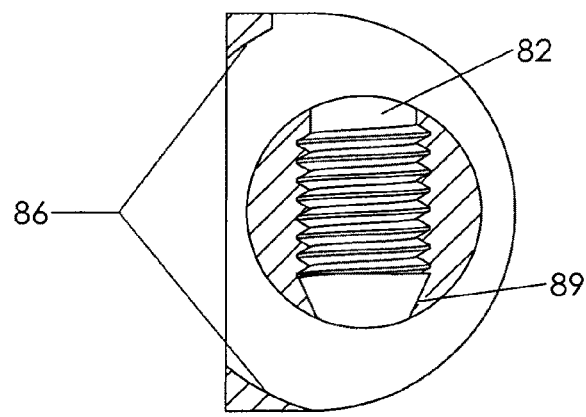

Referring to FIG. 12, the minor diameter 143S of the socket 141 is equivalent to the diameter of the lead portion 128 of shaft 125. This equivalence allows the lead portion 128 to act as a guide to avoid misthreading of the ratcheting mechanism. As the leading edge of the ratchet 127 located on shaft 125 of the cross-post 120 enters socket 141 of collar 140 the slot 149 allows the collar 140 to expand until the first ratchet step is fully encapsulated by the socket 141 situated within the major diameter 143L. With the ratchet diameter 127 accommodated by the large diameter 143L of the socket 141 the expandable collar 140 returns to its neutral position.

While a wide variation of ratchet profiles may be use, the use of a triangular ratchet profile creates a unidirectional locking mechanism which is engaged via compression of the two portions of the ratchet towards each other using a specialized installation tool 171 capable of imparting the necessary medial force. The installation tool 171 contacts each complementary plate at the indentations 62, 92, 152 located on both distal ends or on the stopper 150 located within the female portion 30, 50, 70, 100 of unused interlocks. This feature allows for rapid connection of the contralaterally located cross-post plate 20 and locking plate 40.

The slot 149 which allows the expansion of collar 140 necessary for the operation of the ratchet mechanism also serves as a simple removal method for the device 19. Through the use of a tool, with an end similar to a slotted screw driver, inserted into slot 149 the collar 140 can be expanded past the diameter of the ratcheted teeth 127 found on the shaft 125 of the cross-post 120.

When sufficient expansion is reached the ratcheting mechanism is disengaged and the unidirectional lock is released allowing the cross-post plate 20 and the locking plate 40 to be separated. A semi-circular opening 56 is present on the posterior facing surface 40S of the locking plate 40 in order to have access to the slot 149. In order for slot 149 to be accessible it needs to be visible within the semi-circular opening 56 at all times. The expandable collar 140 must thus be allowed to move in freely along the surface 46 of socket 45 but not allowed to rotate about its principle axis. The necessary motion restriction is accomplished through the interaction of the upper half 145 of the collar 140 and the hexagonal opening 134 of the restriction washer 130. With particular reference to FIGS. 7A, 7B, 7C and 9A, 9B and 9C, the hexagonal extrusion 132 has a minor diameter 131 which is larger than the maximum diameter of the upper portion 145 of the collar 140 located at the vertical segment 144. While a preferred embodiment of the invention involves the use of hexagonal profiles, other profiles may be used.

The difference between the minor diameter 131 of hexagonal extrusion 132 and the maximum diameter of the upper portion 145 of the collar 140 enables the hexagonal extrusion 132 to enclose the upper portion 145 of the collar 140. This arrangement creates a system for restricting the rotational motion of the collar 140. This is accomplished when the sharp corners of the vertical segment 144 on the upper half 145 of the collar 140 are forced into contact with the inner wall 132I of the hexagonal extrusion 132. This occurs if the collar 140 attempts to rotate such that the slot 149 is not visible within the semi-circular opening 56 of the locking plate 40. The above noted diameter difference which allows the interaction between the restriction washer 130 and the collar 140 has been set such that the collar 140 has some play to rotate both clock-wise and counter clock-wise about the principle axis of the collar 40 without slot 149 moving outside the view of the semi-circular window 56 of the locking plate 40.

With rotation of the expandable collar 140 about its principal axis restricted, the three rotational degrees of freedom the collar 140 experiences while moving along the surface 46 of socket 45 that is necessary for correct engagement of the ratcheting mechanism present between the cross-post 120 and the collar 140 must be maintained. This freedom of motion is maintained through the height relationships between the hexagonal extrusion 132 and the hexagonal upper half 145 of collar 140. The counter bores 136 of the washer 130 are aligned with threaded holes 58 of the locking plate 40 and countersinks 138 fasten the restriction washer such that the medial surface 130M is coincident with the lateral surface 40L of the locking plate 40. The use of countersinks minimizes the overall thickness of device 19 reducing the required surgical exposure needed for installation. With the washer 130 in place the opening 134 is concentric with socket 45.

The major diameter 133 of the hexagonal extrusion 132 is less than the maximum diameter 42 of the socket 45. The diameter difference allows the hexagonal extrusion 132 to be situated completely within socket 45 extending to a sufficient depth to permit the previously described interaction with the vertical portion 144 of the upper half 145 of collar 140. The upper half 145 is split into two parts with the top portion 146 being drafted at an angle with respect to the vertical portion 144. The drafted portion 146 is angled toward the center of socket 141 of collar 140 to allow the collar 140 to move along the surface 46 of the socket 45, while preventing the outer wall 144E, 146E from contacting the inner surface 132I of the opening 134.

The height of the hexagonal feature 145 of the collar 140 provided by the drafted portion 146 is necessary to restrict movement along the surface 46 of the socket 45. The draft prevents the upper surface 145L of the collar 140 from moving below the lower surface 132M of the hexagonal extrusion 132 of the washer 130. Rotational restriction at angles beyond which the slot 149 would move outside the semi-circular 56 is provided by the interaction between the hexagonal protrusion 132 and the hexagonal upper portion 145 of the collar 140.

The drafted portion 146 of the collar 140 permits the collar 140 to move smoothly along the surface 46 of socket 45 with a range of motion equivalent to the chosen draft angle. If the motion attempts to exceed the draft angle the outer surface 146E of the drafted portion 146 will contact the inner surface 132I of opening 134 which will impede further motion ensuring the rotational restriction is never compromised.

The extendibility of the device permitting multilevel fusion is shown in FIG. 3. Each individual level of the fusion device 18 comprises two contralateral plates connected by a cross-post 120. Every plate of the device 18 has a flared shaped with a thinner medial portion and thicker distal ends to accommodate multilevel extension through the interlock mechanism of the construct. The interlock mechanism connects adjacent levels through the addition of the cross-post extension plate 60 and the locking extension plate 90 (FIGS. 13A, 13B, 13C, 13D, 14A, 14B, 14C).

Figure 14A:
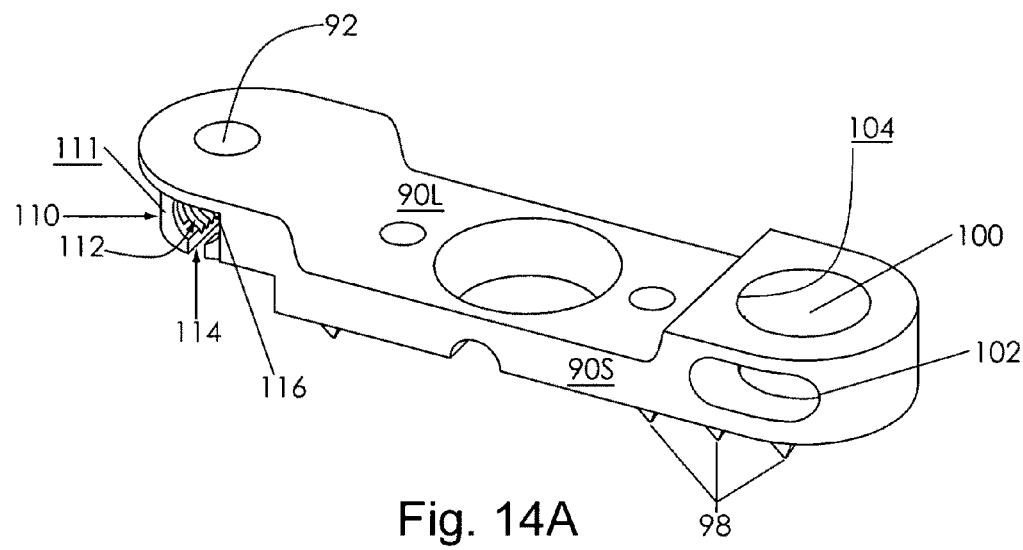
FIGS. 14A, 14B and 14C shows detailed views of the extension locking plate and the male and female portions of the interlocking mechanism.
Figure 14B:
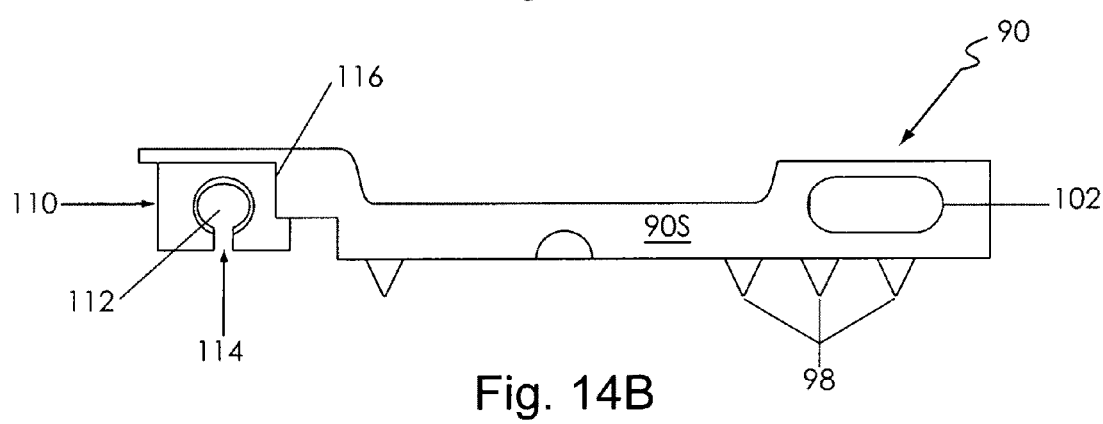
Figure 14C:
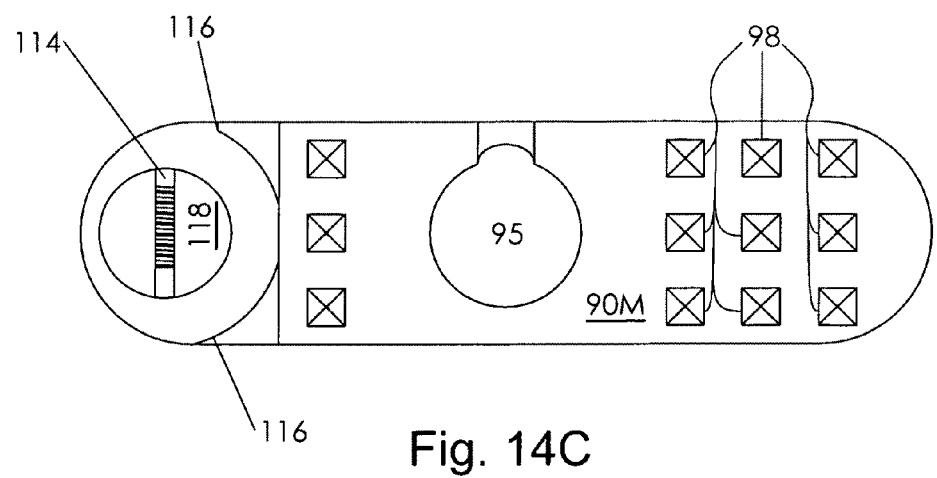
Figure 15A:
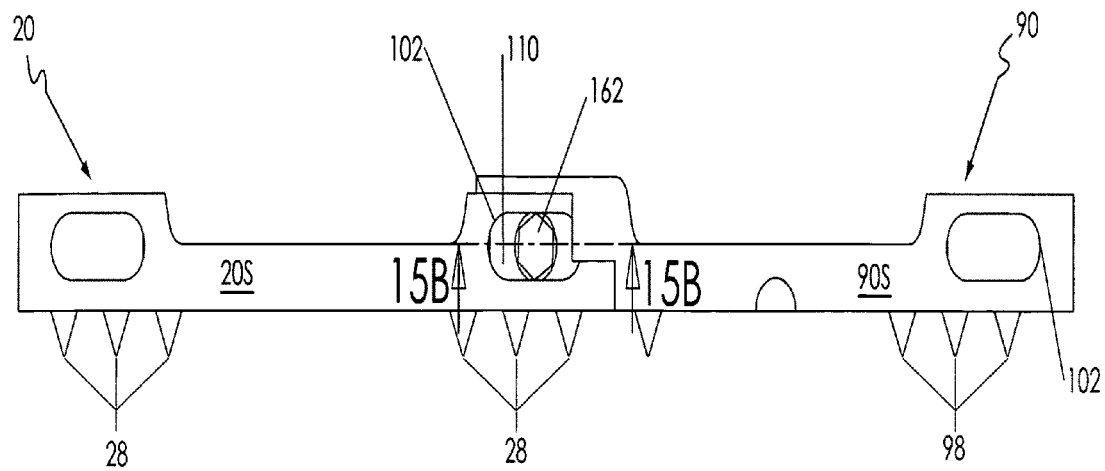
FIG. 15A is a posteriorly orientented view of a pair of interlocked plates with FIG. 15B showing a section taken through the axis of the set screw and viewed in a plane containing the axis of the set screw and perpendicular to the medial surface of the plates and viewed in the direction of the arrows 15B-15B in FIG. 15A.
Figure 15B:
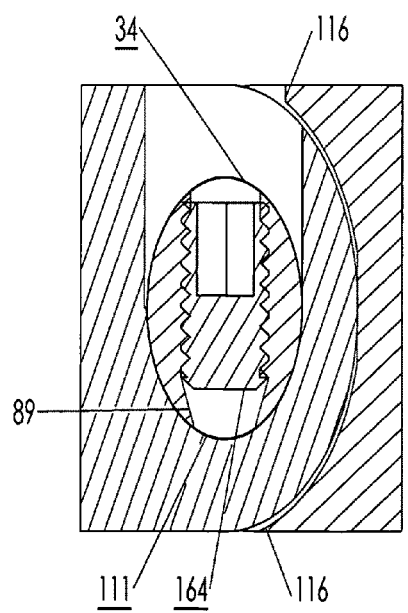

FIGS. 13A, 13B, 13C and 13D show detailed views of an extension cross-post plate 60 and the male and female portions of the interlocking mechanism, while FIGS. 14A, 14B and 14C show detailed views of the extension locking plate 90 and the male and female portions of the interlocking mechanism. FIG. 15A is a posteriorly oriented view of a pair of interlocked plates with FIG. 15B showing a section taken through the axis of the set screw and viewed in a plane containing the axis of the set screw and parallel to the medial surface 60M, 90M of the plates 60, 90 and viewed in the direction of the arrows 15B-15B in FIG. 15A.

Referring to FIGS. 5A to 15B inclusive, the interlocking mechanism includes both a male 80, 110 and female portion 30, 50, 70, 100 that once connected can be adjusted to accommodate the native curvature of the spine with respect to the sagittal plane (kyphosis/lordosis). The male and female portions may be connected together by sliding the male portion into the female portion, and compressing the extension plates onto the spinous process or laminae.

In a preferred embodiment, the male and female portions include an interlock mechanism to further lock the extension plate in place. The principle behind the interlock is the application of a set screw to create a tight, continuous, friction fit between the male interlock 80, 110 and the female interlock 30, 50, 70, 100. The male half of the interlock 80, 110 comprises a cylindrical extrusion having a taper threaded through hole 82, 112 which houses the set screw 160. In a neutral position the set screw 160 is contained entirely within the perimeter of the male interlock 80, 110. The female interlock 30, 50, 70, 100 is comprised of a circular opening with a depth equivalent to the height of the male interlock 80, 110. The second feature of the female interlock 30, 50, 70, 100 is the rectangular access window 32, 52, 72, 102 located on the posterior surfaces 20S, 40S, 60S, 90S of the cross-plate 20, locking plate 40, cross-post extension plate 60, and locking extension plate 90 respectively. With particular reference to FIGS. 15A and 15B, when the male interlock 80, 110 is inserted into the female interlock 30, 50, 70, 100 the head 162 of the set screw 160 can be reached through the access window 32, 52, 72, 102.

Access to the set screw 160 is limited by the width of the access window 32, 52, 72, 102 thus defining a range of possible sagittal orientations of adjacent plates with respect to one another. To ensure the set screw 160 is accessible through the access window 32, 52, 72, 102 restriction walls 86, 116 have been included in the male interlock 80, 110. The restriction walls 86, 116 will create an interference with the posterior surface 20S, 40S, 60S, 90S of the cross-plate 20, locking plate 40, cross-post extension plate 60, and locking extension plate 90 respectively hindering the ability of the set screw head 162 to rotate out of view of the access window 32, 52, 72, 102.

With the male interlock 80, 110 placed within the female interlock 30, 50, 70, 100 and the set screw 160 accessible through the access window 32, 52, 72, 102 the connected plates can be oriented at any angle in the sagittal plane along the possible range of positionings defined by the width of the access window 32, 52, 72, 102 thus accommodating the native curvature of the spine. In order to lock the plates at the desired angle the set screw 160 is tightened into the taper threaded through hole 82, 112. As the set screw 160 is driven through the male interlock 80, 110 the distal surface 164 of the set screw 160 will begin to apply a force on the inner wall 34, 54, 74, 104 resulting in a friction fit.

To further enhance the strength of the friction fit the male interlock 80, 110 has a division 84, 114 on the bottom surface 88, 118. The division extends from the bottom surface 88, 118 to the taper threaded through hole 82, 112. As the set screw is driven toward the inner wall 34, 54, 74, 104 of the female interlock 30, 50, 70, 100 it forces the male interlock 80, 110 to expand radially due to the taper of the thread 89. This expansion is made possible by the division 84, 114 and causes the outer surface 81, 111 of the male interlock 80, 110 to interfere with the inner wall 34, 54, 74, 104 of the female interlock 30, 50, 70, 100. The use of a set screw inspired design allows for locking of adjacent plates along a continuous arc yielding a generalized device that can be applied across varied geometries and morphologies of the posterior elements of the spine at different vertebral levels.

The single level device 19 which includes the cross-post plate 20 and the locking plate 40 have female interlocks 30 and 50, respectively, at both ends. The inclusion of a female interlock 30, 50 at both ends of these single level plates 20, 40 allows the construct to be extended to a multi-level fusion in both the superior and inferior direction. Furthermore, contrary to the male interlocks 80, 110 the female portions of the interlock 30, 50, 70, 100 have embedding teeth 28, 48, 68, 98 on the medial surfaces 20M, 40M, 60M, 90M allowing anchorage of the device on the spinous processes and/or lamina of the posterior vertebral arch. Hence, in the case of the single level fusion device 19 it includes two female interlocks in order to have purchase of the cortical bone of both the superior and inferior posterior elements of the fusion.

When initial installation of the device 18, 19 is complete all distal ends of the construct will have female interlocks 30, 50, 70, 100 present to allow for future extension the implant using the cross-post extension plate 60 and the locking extension plate 90. In order to protect the free female interlocks 30, 50, 70, 100 from unwanted tissue matter that could effect the efficacy of the interlock at some future time a stopper 150 (see FIGS. 10A and 10B) will be placed into each unused female interlock 30, 50, 70, 100. The stopper 150 fits directly into the female interlock 30, 50, 70, 100 in the same manner as the male interlock 80, 110. The stopper 150 has a threaded through hole 156 which in its neutral position houses a set screw 160 entirely within its perimeter. When the stopper 150 is placed into the female interlock 30, 50, 70, 100 the setscrew 160 can be reached via the access window 32, 52, 72, 102. Unlike the male interlock 80, 110 the threaded through hole 156 of the stopper 150 is not tapered. The contact between the distal surface 164 of the set screw 160 and the inner wall 34, 54, 74, 104 of the female interlock 30, 50, 70, 100 holds the stopper in place. The stopper has a graded lip 154 which extends past the female interlock 30, 50, 70, 100 to permit easy removal of the stopper 150 in situ if the construct needs to be extended for further fusion.

The embodiment as described above is not meant to be restricted to any particular region of the spine. The varying morphology and dimensions of the posterior elements, and more specifically the spinous processes and laminae, requires the system to be provided in a wide range of sizes. In the cervical spine where the interspinous process gap is narrow smaller plate sizes and cross-post diameters will be required while in the larger, higher load bearing lumbar spine longer plates are necessary to span two adjacent vertebrae as well as ensure the structural integrity of the device under these higher loads. Intermediate plate and cross-post sizes will service the relatively immobile thoracic region of the spine. To ensure sufficient selection for the wide range of spinal morphologies present in the patient population the system will be provided as a kit having various plates and cross-post sizes capable of performing a multi-level fusion in any one region or combination of regions in the spine.

Figure 16:
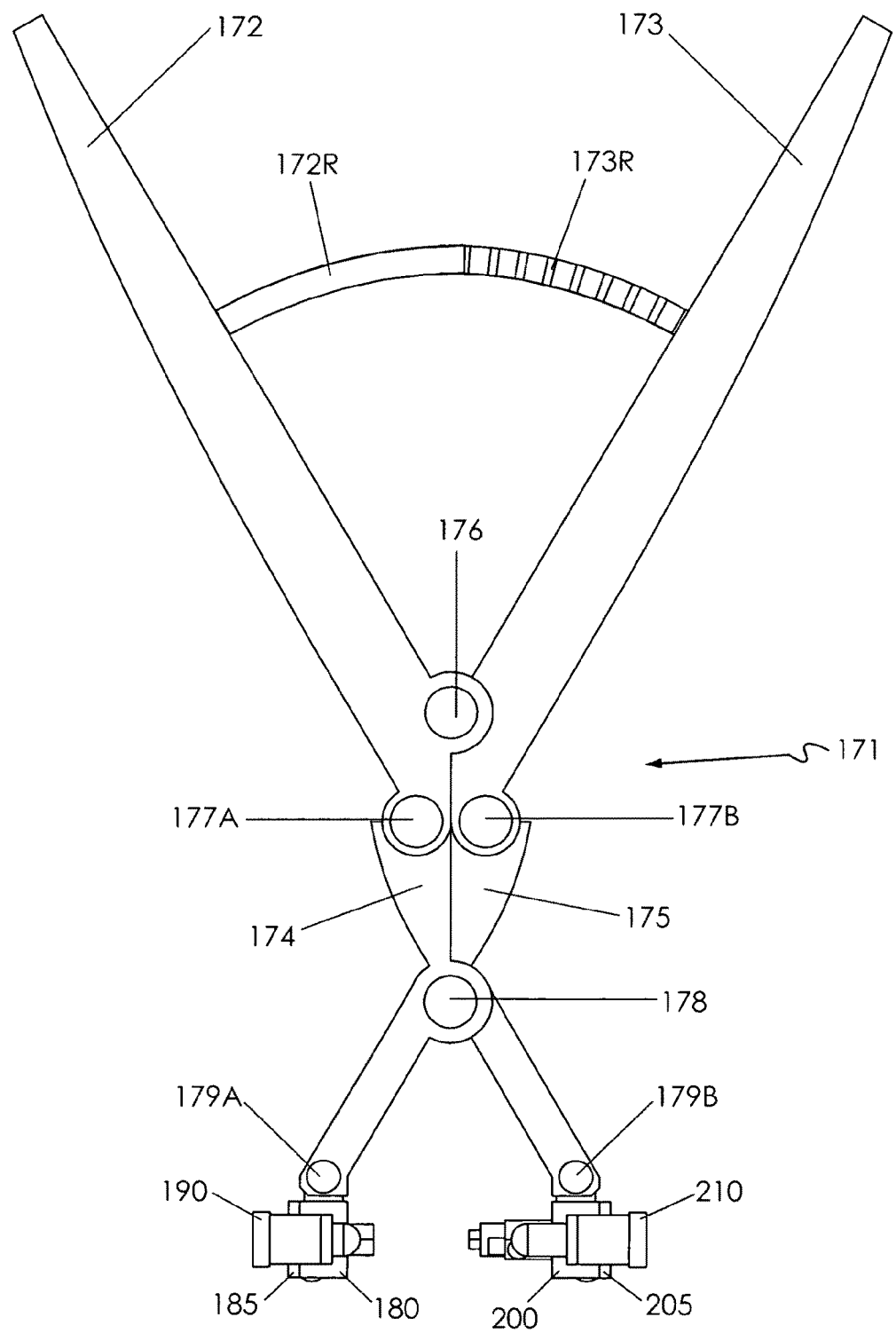
FIG. 16 shows a compression tool for pre-loading and installing a pair of interlocking plates.

Referring to FIG. 16 each single level of the construct, as embodied in FIG. 4, will be installed on the spinous processes and/or laminae of the spine via a uniquely designed compression tool. This tool will be pre-loaded with all components of a single level device prior to placement in situ for final alignment and application of the plates 20, 40, 60, 90 on the spine. The initial loading conditions means there will be no small free-floating components of the device which can be dropped or lost within the patient during installation. This provides the most rapid and efficient implementation with the least amount of risk to the patient.

The installation tool 171 is specifically tailored to apply the necessary medially directed force while accommodating all the geometric freedoms and constraints required for the complementary plates 20, 40 to lock at varying angles in both the axial and coronal planes. Stated in other terms, the installation tool allows ±25 degrees of rotation about the axis perpendicular to the posterior face 20S, 40S of the plates 20, 40 and passing through the spherical origin of the socket 25, 45 of the plates 20, 40; similarly ±25 degrees of rotation is permitted about the principal longitudinal axis of the plates 20, 40.

The installation tool 171 is comprised of two handles 172, 173 pinned 176 together at a distance along the principal axis. Inferior to pin 176 are two leverage arms 174, 175 that are pinned 177A, 177B to each respective handle 172, 173 and to each other at pin 178. At the inferior most portion of each leverage arm are pinned 179A, 179B contact pieces 180, 200 specific to either the cross-post plate 20 or the locking plate 40. The installation tool 171 is preloaded with all components of the single level device 19 attached to the appropriate contact piece 180, 200.

Each contact piece 180, 200 contains a poly-axial arm 190, 210 protruding away from the principal axis of the installation tool 171. The poly-axial arms 190, 210 are associated with contact pieces 180, 200 respectively via ball and socket joints. The spherical portion 190S, 210S of the poly-axial arms 190, 210 are seated in the spherical sockets 183, 203 of contact pieces 180, 200 respectively; the radii of curvature of the spherical portion 190S, 210S and the spherical socket 183, 203 are identical to allow for smooth interaction between the components. The spherical portions 190S, 210S of the poly-axial arms 190, 210 remain contained within the contact pieces 180, 200 due to restriction caps 185, 205 found on the outbound surface of the contact pieces 180, 200. The restriction caps 185, 205 contain holes 185H, 205H allowing the remainder of the poly-axial arms 190,210 to reside outside the contact pieces 180,200. The holes 185H, 205H in the restriction caps 185, 205 have a radius small enough to contain the spherical potion 190S, 210S of the poly-axial arms 190, 210 but great enough to allow up to ±25 degrees of motion in both the coronal and axial planes without interference between the restriction caps 185, 205 and the cylindrical posts 190C, 210C of the poly-axial arms 190, 210. The spherical portions 190S, 210S of the poly-axial arms 190, 210 also contains rectangular depressions 190R, 210R of a given depth and subtending a small arc of the spherical portion 190S, 210S. The planar surface 190P, 210P of the rectangular depression 190R, 210R faces the inferior most surface 180I, 200I of the contact pieces 180,200. Through holes 187,207 pass from the inferior most surfaces 180I, 200I of the contact pieces 180, 200 and into the spherical socket 183, 203 of the contact pieces 180, 200. A pin 188, 208 of a given height is placed in this hole 187, 207 and extends into the rectangular depression 190R, 210R of the spherical portion 190S, 210S of the poly-axial arm 190, 210. The diameter of the pin 188, 208 is smaller than the width of the rectangular depression 190R, 210R allowing for minimal play, restricting rotation of the poly-axial arm 190, 210 in the sagittal plane; a constraint that ensures the complementary plates 20, 40 of a single level do not deviate more than ±5 degrees with respect to each other in the sagittal plane. Furthermore, the depth of penetration of pin 188, 208 is less than the distance between the planar face 190P, 210P of the rectangular depression 190R, 210R and the inferior most surface 180I, 200I of the contact piece 180, 200. The gap created between the pin 188, 208 and the planar face 190P, 210P of the rectangular depression 190R, 210R permits ±25 degrees of rotation in the coronal and axial planes.

The cylindrical posts 190C, 210C attached to the spherical portion 190S, 210S of the poly-axial arm 190, 210 extend outwards from the contact pieces 180, 200. Located at the distal end of the cylindrical posts 190C, 210C are planar surfaces 190M, 210M respectively. Bilaterally, at each distal end of the planar surface 190M, 210M angled arms 192A, 192B, 212A, 212B extend towards the principal axis of the installation tool 171. The angle of the arms 192A, 192B, 212A, 212B allows the poly-axial arms 190,210 to rotate in the axial and coronal planes without interference from the contact pieces 180, 200. At the distal ends of the angled arms 192A, 192B, 212A, 212B cylindrical posts 194A, 194B, 214A, 214B continue to towards the principal axis of the installation tool 171 as extensions of the angled arms 192A, 192B, 212A, 212B. The principal axis of the cylindrical posts 194A, 194B, 214A, 214B runs perpendicular to the planar surface 190M, 210M of the poly-axial arms 190, 210. The distal end of the cylindrical posts 194A, 194B, 214A, 214B extend past the inboard surface 180M, 200M of the contact pieces 180, 200 and preferably terminates in hemi-spherical heads 196A, 196B, 216A, 216B. In another embodiment, the cylindrical posts may terminate in a non-hemispherical profile.

Referring to FIGS. 17A, 17B, 17C, 17D, the cross-post 120 and cross-post plate 20 are loaded on to contact piece 180. The hexagonal extrusion 182 located on the inboard surface 180M of the contact piece 180 engages the hexagonal depression 129 in the proximal planar surface 123 of the cross-post 120. The engagement of the hexagonal features of the contact piece 180 and the cross-post 120 fixes the principal axis of the cross-post 120 leaving the cross-post plate 20 free to move along the spherical surface 122 of the cross-post 120. The height of the hexagonal extrusion 182 of the contact piece 180 is such that when fully engaged with the hexagonal depression 129 of the cross-post 120 there remains a sufficient gap between the inboard surface 180M of the contact piece 180 and the cross-post plate 120 to allow ±25 degrees of rotation in the coronal and axial planes without interference from any other portion of the installation tool 171.

Figure 18A:
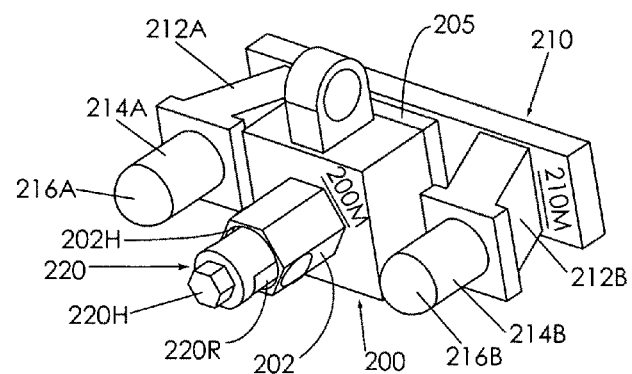
FIGS. 18A, 18B and 18C show detailed views of second contact piece with polyaxial arm that supports an interlocking plate during compression.
Figures 18B, 18C:
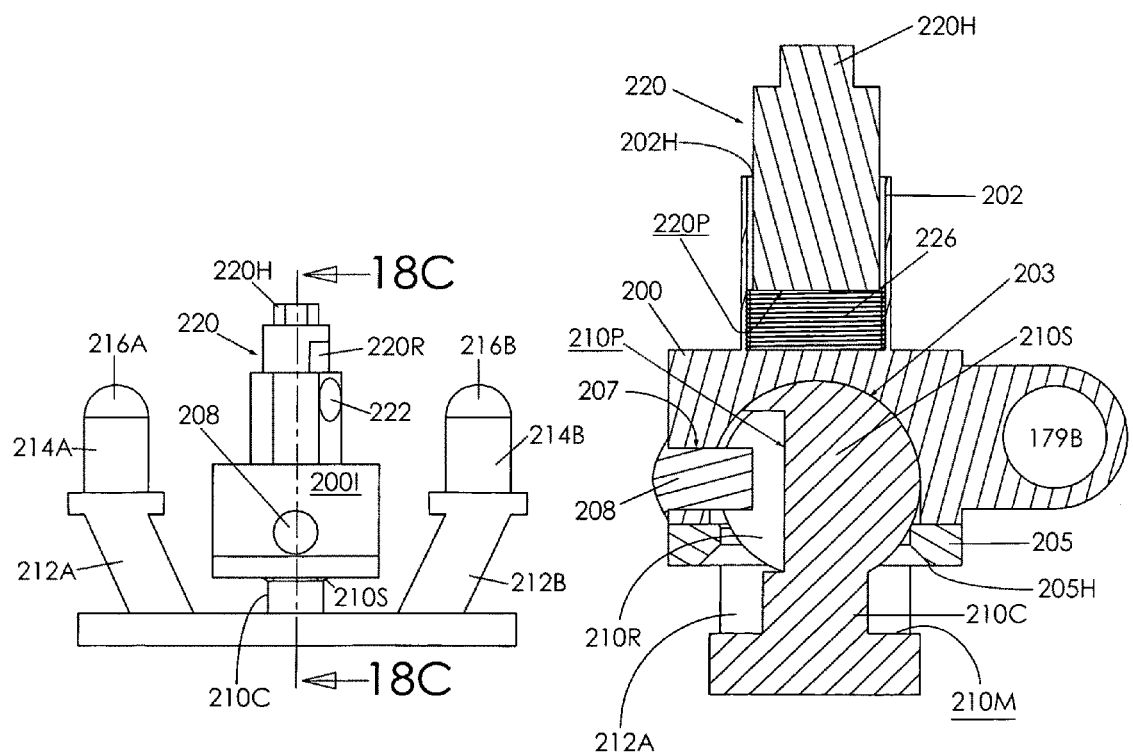

Referring to FIGS. 18A, 18B, 18C, the locking plate 40 containing the expandable collar 140 is loaded on to contact piece 200. The cylindrical guide post 220 projecting from the inbound surface 200M of the contact piece 200 towards the principal axis of the installation tool 171 passes through the socket 141 of the expandable collar 140, acting as a guide for the expandable collar 140. The cylindrical guide post 220 fixes the principal axis of the expandable collar 140 leaving the locking plate 40 free to move along the spherical surface 46 of said plate 40. The cylindrical guide post's 220 proximal end is inscribed within hexagonal extrusion 202 found on the inboard surface 200M of the contact piece 200. Between the proximal surface 220P of the cylindrical guide post 220 and the inboard surface 200M of the contact piece 200 there is placed a spring 226 which when compressed allows the cylindrical guide post 220 to retreat further into the hexagonal extrusion 202. The cylindrical guide post 220 is maintained in the hexagonal extrusion 202 via pin 222 running through the side of the hexagonal extrusion 202 and into rectangular depression 220R of the cylindrical guide post 220. The diameter of the bore hole 202H that houses the cylindrical guide post 220 and spring 226 has diameter equal in size to the diameter 127 of the ratcheted teeth of the cross-post 120; this enables the hexagonal extrusion 202 of the contact piece 200 to house both the cylindrical guide post 220 and the cross-post 120. Furthermore, the hexagonal extrusion 202 is only marginally larger than the hexagonal feature 145 of the expandable collar 140. The size of hexagonal extrusion 202 of the contact piece 200 allows said feature to pass through opening 134 of the restriction washer 130 permitting hexagonal extrusion 202 to make direct contact with the hexagonal feature 145 of the expandable collar 140 permitting hexagonal extrusion 202 to apply force to expandable collar 140.

When both the cross-post plate 20 and the locking plate 40 are loaded on to their respective contact pieces 180, 200. The hexagonal depression 121 on the distal surface 120M of the cross-post 120 is engaged with the hexagonal extrusion 220H of the cylindrical guide post 220 of the contact piece 200. The engagement of the cylindrical guide post 220 and the cross-post 120 force the expandable collar 140 to be aligned correctly with the cross-post 120 as to avoid misthreading of unidirectional ratcheting steps.

At the time of installation of each individual plate 20, 40, 60, 90, all female interlocks 30,50,70,100 will contain stoppers 150. Each of these stoppers 150 contains a spherical indentation 152 on its superior surface 158; the radius of curvature of these indentations 152 is equal to the radius of curvature of the hemi-spherical heads 196A, 196B, 216A, 216B found on the distal ends of the cylindrical posts 194A, 194B, 214A, 214B of the poly-axial arms 190, 210. This equivalent radius of curvature allows the hemi-spherical heads 196A, 196B, 216A, 216B to make contact with the stoppers 150 at varying angles with respect to the superior surface 158 of the stopper 150. In the case of installing an extension level of the device, the cross-post extension plate 60 and the locking extension plate 90 both have similar spherical indentations 62, 92 on their outboard surfaces 60L, 90L directly above the male interlocks 80, 110. The placement of the spherical indentations 62, 92 on the extension plates 60, 90 allows us to treat said plates 60, 90 as identical to stoppers 150 placed in the female interlocks 30, 50.

In both the single level cross-post plate 20 and the extension cross-post plate 60, the longitudinal and height difference between the central outboard surface 20L, 60L and the spherical indentations 62, 152 of either the stopper 150 or the outboard surface directly above the male interlock 80 remains constant. The same consistency exists between the spherical indentations 92, 152 of either the stopper 150 or the outboard surface above the male interlock 110 of extension locking plate 90 and the central outboard surface 40L, 90L of the locking plate 40 or the extension locking plate 90. When plates 20, 40, 60, 90 are correctly loaded into the respective contact pieces 180, 200 the locations of all related spherical indentations 62, 92, 152 are fixed in space relative to the loading points 182, 202 of the contact pieces 180, 200.

The cylindrical posts 194A, 194B, 214A, 214B found extending towards the principal axis of the installation tool 171 from the angled arms 192A, 192B, 212A, 212B of the poly-axial arm 190, 210 is of a length such that the apex of the hemi-spherical head 196A, 196B, 216A, 216B projects a given distance past the location of the spherical indentations 62, 92, 152. Thus, when compression is applied to the cross-post 120 and the expandable collar 140 by the hexagonal extrusions 182, 202 of the respective contact pieces 180, 200 a compressive force at the cylindrical posts 194A, 194B, 214A, 214B projecting from the angled arms 192A, 192B, 212A, 212B of the poly-axial arm 180, 200 is transferred to a force at the cylindrical post 190C, 210C connecting the planar surface 190M, 210M to the spherical portion 190S, 210S of the poly-axial arms 190, 210. This force moves the poly-axial arm 190, 210 away from the principal axis of the installation tool 171 with respect to the contact pieces 180, 200 essentially locking the poly-axial arm 190, 210 into position via contact with the restriction cap 185, 205. The locked poly-axial arm 190, 210 will be oriented identically in 3 dimensional space as the plates 20, 40, 60, 90 allowing compression force to be applied perpendicular to the longitudinal axis of the plate 20, 40, 60, 90.

Taken as a whole, the contact pieces 180, 200 and poly-axial arm 190, 210 allow for the appropriate medially directed force while maintaining the ability of the plates to be placed at varying angles in the coronal and axial planes. Furthermore, the cylindrical guide post 220 engaged with the distal surface 120M of the cross-post 120 guides the unidirectional ratcheting mechanisms. As compression is applied by the installation tool 171 the cylindrical guide post 220 will be driven into the hexagonal extrusion 202 of contact piece 200 compressing the spring 226 also housed within said hexagonal extrusion 202. The bore hole 202H containing the cylindrical guide post is large enough in diameter to accommodate the maximum diameter 127 of the cross-post 120 allowing the cross-post's 120 distal surface 120M to extend past the surface 145L of the expandable collar 140 enabling the minimum distance between the cross-post plate 20,60 and the locking plate 40,90. In order, for the cylindrical guide post 220 to be effective the inboard surfaces 180M, 200M of both contact pieces 180, 200 must remain parallel; this requirement is accomplished via the pinning 179A, 179B of the contact pieces to the leverage pieces at 174, 175. The handle pieces 172, 173 are connected superiorly from pin 176 by a ratchet 172R, 173R providing the user with incremental steps for the compression of the installation tool 171 without the need to maintain the grip force indefinitely throughout the process.

The device is completely revisable in that it can be easily expanded to include more levels or removed with an additional operation. The device can also be expanded to include an attachment to the occipital bone, the atlas and the sacrum. The device is easily adaptable to be used as a fusion extension by connecting to pre-existing hardware devices such as pedicle screw or lateral mass screw constructs with simple connectors. The device can also be used for the correction of scoliosis.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

1. White A A, Panjabi M M. Clinical Biomechanics of the Spine. $2^{nd}$ ed. Philadelphia: J.B. Lippincott Co., 1990

Therefore what is claimed is:

1. A device for stabilizing a portion of a spine, comprising:
   a first pair of longitudinal plates, wherein a medial surface of each plate of said first pair of longitudinal plates is adapted to contact two adjacent spinous processes or laminae when said first pair of longitudinal plates are arranged on contralateral sides of a sagittal plane;
   a post for connecting said first pair of longitudinal plates at an interspinous gap between the two adjacent spinous processes; and
   at least one plate connection means on each plate of said first pair of longitudinal plates for optionally connecting said first pair of longitudinal plates to an additional pair of longitudinal plates in-situ without removal of said post from said first pair of longitudinal plates; and wherein said plate connection means accommodates a kyphotic or lordotic curvature of the spine.

2. The device according to claim 1 wherein:
said first pair of longitudinal plates comprises a first plate and a second plate, each plate including a lateral surface and said medial surface whereby said medial surfaces face each other when said pair of longitudinal plates are contacted with the two adjacent spinous processes or laminae;
a proximal end of said post is slidably received through a first aperture in said first plate, said first aperture extending from said lateral surface of said first plate to said medial surface of said first plate; and
said second plate includes a post connection means for connecting said second plate with a distal end of said post.

3. The device according to claim 2 wherein said post and said first aperture are adapted to permit limited polyaxial orientation of said post when said post is received within said first aperture.

4. The device according to claim 3 wherein:
said post comprises a cylindrical shaft intersecting a base wherein a surface of said base forms an intersection with said shaft is a spherical surface;
said first aperture forms a first aperture surface within said first plate;
said first aperture surface is spherical;
a diameter of said first aperture at said medial surface of said first plate is smaller than a diameter of said first aperture at said lateral surface of said first plate,
a radius of curvature of said spherical surface of said base of said post is equal to a radius of curvature of said spherical surface of said first aperture surface; and
a diameter of said first aperture at said medial surface of said first plate is sufficiently large to permit limited polyaxial orientation of said post when said spherical surface of said base is in contact with said first aperture surface.

5. The device according to claim 4 wherein said diameter of said first aperture formed at said intersection of said first aperture with said medial surface of said first plate limits said polyaxial orientation of said post to angles of approximately 20° or less before said shaft of said post contacts said medial surface of said first plate.

6. The device according to claim 4 wherein said base is a truncated hemisphere.

7. The device according to claim 3 wherein:
said second plate includes a second aperture;
said second aperture is spherical and extends from said lateral surface of said second plate to said medial surface of said second plate;
a diameter of said second aperture at said medial surface of said second plate is smaller than a diameter of said second aperture at said lateral surface of said second plate,
said post connection means is a collar comprising a socket that engages with said distal end of said post;
said second aperture houses said collar when said collar is placed within said second aperture from said lateral surface of said second plate;
said collar comprises a lateral annular surface orthogonal to a longitudinal axis of said collar, a cylindrical internal surface, and a spherical external surface;
a radius of curvature of said external surface of said collar is equal to a radius of curvature of said spherical surface of said second aperture surface;
a diameter of said second aperture at said medial surface of said second plate is larger than a diameter of said socket, whereby said collar may extend medially beyond said medial surface of said second plate when said collar engages with said distal end of said post; and
whereby said diameter of said second aperture at said medial surface of said second plate permits polyaxial orientation of said collar when said external surface of said collar is in contact with said second aperture surface.

8. The device according to claim 7 wherein:
an internal thread is included on an inner surface of said collar;
an external thread is included on said post; and
said internal and external threads are configured to engage when said distal end of said post is inserted into said socket of said collar.

9. The device according to claim 8 wherein said collar includes a slot enabling elastic deformation of said collar when said distal end of said post engages with said socket of said collar.

10. The device according to claim 9 wherein an additional aperture is included in said second plate for accessing said slot, whereby a tool can be used to expand said collar and disengage said threads and disconnect said post from said collar.

11. The device according to claim 10 wherein said additional aperture comprises a channel located within said medial surface of said second plate, wherein said channel has a longitudinal direction substantially orthogonal to the spine, and wherein said channel extends from said second aperture to an outer surface of said second plate.

12. The device according to claim 11 wherein:
a restriction washer is attached to said lateral surface of said second plate, said restriction washer positioned to confine said collar within said second aperture in said second plate;
said restriction washer including a central aperture, thus allowing the insertion of the tool for the application of a compressive force to said collar when assembling said device;
said restriction washer further including a first protrusion that projects in a medial direction from a medial surface of said restriction washer into said second aperture;
said protrusion adapted to engage with a second protrusion that projects from said lateral annular surface of said collar;
wherein contact between said first protrusion and said second protrusion restricts an angular orientation of said collar about an axis orthogonal to said lateral surface of said second plate;
whereby said channel may be substantially aligned with said slot and restricted from moving out of alignment.

13. The device according to claim 12 wherein said first and second protrusions are hexagonal protrusions, each of said hexagonal protrusions comprising an outer wall, an inner wall, and a distal surface; and wherein said first hexagonal protrusion has a larger internal diameter than an external diameter of said second protrusion.

14. The device according to claim 13 wherein said second protrusion comprises a primary hexagonal protrusion extending from said lateral surface of said collar, and a secondary hexagonal protrusion extending from said primary hexagonal protrusion, whereby said outer wall of said secondary protrusion is angled towards a center of said collar, whereby limited polyaxial motion of said collar is permitted.

15. The device according to claim 8 wherein said internal and external threads comprise a triangular profile enabling ratcheting action of said post in said collar under a compressive force directed along an axis of said post.

16. The device according to claim 8 wherein:
said post includes a cylindrical lead portion between said external thread and said distal end of said post;
a diameter of said lead portion is equal to a minor diameter of said external thread; and
said diameter of said lead portion is equal to a minor diameter of said internal thread;
whereby said lead portion acts as a guide thereby avoiding misthreading said post into said collar.

17. The device according to claim 2 wherein:
said second plate includes a second aperture;
said second aperture extends from said lateral surface of said second plate to said medial surface of said second plate;
said post connection means is a nut;
said second aperture is further adapted to house said nut when said nut is placed within said second aperture from said lateral surface of said second plate; and
said post includes a thread for engaging said nut.

18. The device according to claim 17 wherein said second aperture limits a rotation of said nut within said second plate.

19. The device according to claim 2 wherein:
said second plate includes a second aperture;
said second aperture extends from said lateral surface of said second plate to said medial surface of said second plate;
said post connection means is a collar comprising a socket that engages with said distal end of said post; and
said second aperture is further adapted to house said collar when said collar is placed within said second aperture from said lateral surface of said second plate.

20. The device according to claim 19 wherein said distal end of said post is engaged with said collar by the application of a compressive force along an axis of said post.

21. The device according to claim 20 wherein said collar and said distal end of said post may be removably attached.

22. The device according to claim 19 wherein:
an internal thread is included on an inner surface of said collar;
an external thread is included on said post; and
said internal and external threads are configured to engage when said distal end is inserted into said socket of said collar under a compressive force directed along an axis of said post.

23. The device according to claim 22 wherein said collar includes a slot enabling elastic deformation of said collar when said distal end of said post engages with said socket of said collar.

24. The device according to claim 1 wherein:
said first pair of longitudinal plates comprises a first plate and a second plate, each plate including a lateral surface and a medial surface whereby said medial surfaces face each other when said pair of longitudinal plates are contacted with the two adjacent spinous processes or laminae;
said medial surfaces of said plates include spikes projecting from said surfaces to penetrate the two spinous processes or laminae, whereby said longitudinal plates may be fixated to the two spinous processes or laminae by application of a suitable compressive force.

25. The device according to claim 1 further comprising said additional pair of longitudinal plates, wherein said plate connection means comprises a female portion located at a one or both distal ends of each plate of said first pair of longitudinal plates, said female portion comprising a cylindrical recess beneath a lateral surface of said each plate of said first pair of longitudinal plates, and wherein:
each plate of said additional pair of longitudinal plates includes a cylindrical male portion provided at first end of each plate of said additional pair of longitudinal plates;
said male portion extends in a medial direction; and
a second end of each plate of said additional pair of longitudinal plates is adapted to contact an additional adjacent spinous process;
whereby said first pair of longitudinal plates may be optionally connected to said additional pair of longitudinal plates by slidably receiving a male portion of a first additional plate of said pair of additional longitudinal plates into said female portion of a first plate of said first pair of longitudinal plates, and slidably receiving a cylindrical male portion of a second additional plate of said pair of additional longitudinal plates into said female portion of a second plate of said first pair of longitudinal plates.

26. The device according to claim 25 wherein said first pair of longitudinal plates is connected to said additional pair of longitudinal plates and wherein said device includes an additional post adapted to connect said additional pair of longitudinal plates within an interspinous gap between the additional spinous process and one of the two adjacent spinous processes.

27. The device according to claim 26 wherein said additional pair of longitudinal plates includes an additional plate connection means for optionally connecting said additional pair of longitudinal plates to a second additional pair of longitudinal plates, wherein:
each plate of said additional pair of longitudinal plates further includes a female portion located at said second end of each plate of said additional pair of longitudinal plates, said female portion comprising a cylindrical recess beneath a lateral surface of said each plate of said additional pair of longitudinal plates; and
each plate of said second additional pair of longitudinal plates is adapted to contact a spinous process adjacent to the additional spinous process when said second additional pair of longitudinal plates is connected to said additional pair of longitudinal plates and when said second additional pair of longitudinal plates is arranged on contralateral sides of said sagittal plane.

28. The device according to claim 27 wherein:
each male portion in said additional pair of longitudinal plates and said second additional pair of plates includes a cylindrical aperture with an internal thread therein, and where an axis of said cylindrical aperture is parallel to a lateral surface of said each plate, orthogonal to a longitudinal axis of said each plate, and orthogonal to an axis of said cylindrical male portion in said each plate;
each cylindrical aperture further includes a distal tapered segment and a slot parallel to an axis of said cylindrical aperture, said slot forming an opening in said cylindrical aperture on a medial surface of said male portion;
each female portion in each of said first pair of longitudinal plates, said additional pair of longitudinal plates, and said second additional pair of longitudinal plates includes an access window forming an aperture in a side of said each plate extending into said female portion, where an axis perpendicular to a plane of said access window is parallel to a lateral surface of said each plate, orthogonal to a longitudinal axis of said each plate, and orthogonal to an axis of said female portion in said each plate;

wherein each male portion may be connected to each female portion by a set screw inserted through said access window, whereby said set screw causes said each male portion to expand and frictionally engage said each female portion.

29. The device according to claim 28 wherein:

one or more additional pairs of longitudinal plates are serially connected to said first pair of longitudinal plates;

each of said one or more additional pairs of longitudinal plates is connected by a post within an interspinous gap; and said serial connection of said one or more additional pairs of longitudinal plates allows for locking of adjacent pairs of plates along a continuous arc, yielding a device that can accommodate varying geometries and morphologies of posterior vertebral elements of the spine at different vertebral levels.

30. The device according to claim 25 wherein:

each male portion in said additional pair of longitudinal plates includes a cylindrical aperture with an internal thread therein, and where an axis of said cylindrical aperture is parallel to a lateral surface of said each plate, orthogonal to a longitudinal axis of said each plate, and orthogonal to an axis of said cylindrical male portion in said each plate;

each cylindrical aperture further includes a distal tapered segment and a slot parallel to an axis of said cylindrical aperture, said slot forming an opening in said cylindrical aperture on a medial surface of said male portion;

each female portion in each of said first pair of longitudinal plates includes an access window forming an aperture in a side of said each plate extending into said female portion, where an axis perpendicular to a plane of said access window is parallel to a lateral surface of said each plate, orthogonal to a longitudinal axis of said each plate, and orthogonal to an axis of said cylindrical recess in said each plate;

wherein each male portion may be connected to each female portion by a set screw inserted through said access window, whereby said set screw causes said each male portion to expand and frictionally engage said each female portion.

31. The device according to claim 30 wherein:

each female portion in said first pair of plates optionally contains a cylindrical stopper including a cylindrical aperture with an internal thread therein, and where an axis of said cylindrical aperture is parallel to a lateral surface of said each plate, orthogonal to a longitudinal axis of said each plate, and orthogonal to an axis of said female portion in said each plate; and each stopper may be connected to each female portion by a set screw inserted through said access window, whereby said set screw causes said each stopper to frictionally engage said each female portion;

whereby said stopper includes a means for removing said stopper prior to connecting said first pair of longitudinal plates to said additional pair of longitudinal plates.

32. The device according to claim 31 wherein said stopper is configured to prevent an accumulation of unwanted tissue matter within said female portion when said first pair of plates are implanted in a patient.

33. The device according to claim 31 wherein said means of removing said stopper is a raised lip located on a lateral surface of said stopper, wherein said lateral surface is externally accessible when said stopper is inserted in said female portion.

34. The device according to claim 25 wherein:

each male portion in each plate of said additional pair of longitudinal plates includes a cylindrical aperture with an internal thread therein, and where an axis of said cylindrical aperture is parallel to a lateral surface of said each plate, orthogonal to a longitudinal axis of said each plate, and orthogonal to an axis of said cylindrical male portion in said each plate;

each female portion in each plate of said first pair of longitudinal plates includes an access window forming an aperture in a side of said each plate extending into said female portion, where an axis perpendicular to a plane of said access window is parallel to a lateral surface of said each plate, orthogonal to a longitudinal axis of said additional plate, and orthogonal to an axis of said female portion in said each plate;

wherein each male portion may be connected to each female portion by a bolt, whereby a shaft of said bolt passes through said access window and engages said internal thread in said cylindrical aperture.

35. The device according to claim 25 wherein said female portion is located at both distal ends of each of said plate of said first pair of longitudinal plates, wherein each plate of said additional pair of longitudinal plates may be adapted to contact an additional superior or inferior adjacent spinous process when said additional pair of longitudinal plates is connected to said first pair of longitudinal plates.

36. A device for stabilizing a portion of a spine, comprising:

a first plate and a second plate, each plate including a lateral surface and a medial surface whereby said medial surfaces face each other when said plates are contacted with two adjacent spinous processes or laminae;

a post for connecting said first plate and said second plate at an interspinous gap between the two adjacent spinous processes, wherein a proximal end of said post is slidably received through a first aperture in said first plate, said first aperture extending from said lateral surface of said first plate to said medial surface of said first plate; and a collar adapted to connect to a distal end of said post, wherein said collar is housed within a second aperture in said second plate;

wherein said post and said first aperture are adapted to permit limited polyaxial orientation of said post when said post is received within said first aperture and wherein said collar and said second aperture are adapted to permit limited polyaxial orientation of said collar when said collar is housed within said second aperture; and at least one plate connection means on each plate of said first plate and said second plate for optionally connecting said first plate and said second plate to an additional pair of longitudinal plates in-situ without removal of said post from said first plate and said second plate.

37. The device according to claim 36 wherein:

said second aperture is spherical and extends from said lateral surface of said second plate to said medial surface of said second plate;

a diameter of said second aperture at said medial surface of said second plate is smaller than a diameter of said second aperture at said lateral surface of said second plate, said collar includes a socket that engages with said distal end of said post;

said second aperture houses said collar when said collar is placed within said second aperture from said lateral surface of said second plate;

said collar comprises a lateral annular surface orthogonal to a longitudinal axis of said collar, a cylindrical internal surface, and a spherical external surface;

a radius of curvature of said external surface of said collar is equal to a radius of curvature of said spherical surface of said second aperture surface;

a diameter of said second aperture at said medial surface of said second plate is larger than a diameter of said socket, whereby said collar may extend medially beyond said medial surface of said second plate when said collar engages with said distal end of said post; and whereby said diameter of said second aperture at said medial surface of said second plate permits polyaxial orientation of said collar when said external surface of said collar is in contact with said second aperture surface.

38. The device according to claim 37 wherein:

an internal thread is included on an inner surface of said collar;

an external thread is included on said post; and said internal and external threads are configured to engage when said distal end of said post is inserted into said socket of said collar.

39. The device according to claim 38 wherein:

said post includes a cylindrical lead portion between said external thread and said distal end of said post;

a diameter of said lead portion is equal to a minor diameter of said external thread; and said diameter of said lead portion is equal to a minor diameter of said internal thread;

whereby said lead portion acts as a guide thereby avoiding misthreading said post into said collar.

40. The device according to claim 39 wherein said internal and external threads comprise a triangular profile enabling ratcheting action of said post in said collar under a compressive force directed along an axis of said post.

41. The device according to claim 40 wherein said collar includes a slot enabling elastic deformation of said collar when said distal end of said post engages with said socket of said collar.

42. The device according to claim 41 wherein an additional aperture is included in said second plate for accessing said slot, whereby a tool can be used to expand said collar and disengage said threads and disconnect said post from said collar.

43. The device according to claim 42 wherein said additional aperture comprises a channel located within said medial surface of said second plate, wherein said channel has a longitudinal direction substantially orthogonal to the spine, and wherein said channel extends from said second aperture to an outer surface of said second plate.

44. The device according to claim 43 wherein:

a restriction washer is attached to said lateral surface of said second plate, said restriction washer positioned to confine said collar within said second aperture in said second plate;

said restriction washer including a central aperture, thus allowing the insertion of the tool for the application of a compressive force to said collar when assembling said device;

said restriction washer further including a first protrusion that projects in a medial direction from a medial surface of said restriction washer into said second aperture;

said protrusion adapted to engage with a second protrusion that projects from said lateral annular surface of said collar;

wherein contact between said first protrusion and said second protrusion restricts an angular orientation of said collar about an axis orthogonal to said lateral surface of said second plate;

whereby said channel may be substantially aligned with said slot and restricted from moving out of alignment.

45. The device according to claim 44 wherein said first and second protrusions are hexagonal protrusions, each of said hexagonal protrusions comprising an outer wall, an inner wall, and a distal surface; and wherein said first hexagonal protrusion has a larger internal diameter than an external diameter of said second protrusion.

46. The device according to claim 45 wherein said second protrusion comprises a primary hexagonal protrusion extending from said lateral surface of said collar, and a secondary hexagonal protrusion extending from said primary hexagonal protrusion, whereby said outer wall of said secondary protrusion is angled towards a center of said collar, whereby limited polyaxial motion of said collar is permitted.

47. The device according to claim 36 wherein:

said post comprises a cylindrical shaft intersecting a base wherein a surface of said base that forms an intersection with said shaft is a spherical surface;

said first aperture forms a first aperture surface within said first plate;

said first aperture surface is spherical;

a diameter of said first aperture at said medial surface of said first plate is smaller than a diameter of said first aperture at said lateral surface of said first plate, a radius of curvature of said spherical surface of said base of said post is equal to a radius of curvature of said spherical surface of said first aperture surface; and a diameter of said first aperture at said medial surface of said first plate is sufficiently large to permit limited polyaxial orientation of said post when said spherical surface of said base is in contact with said first aperture surface.

48. The device according to claim 47 wherein said base is a truncated hemisphere.

49. The device according to claim 47 wherein said diameter of said first aperture formed at said intersection of said first aperture with said medial surface of said first plate limits said polyaxial orientation of said post to angles of approximately 20° or less before said shaft of said post contacts said medial surface of said first plate.

50. The device according to claim 36 wherein said medial surfaces of said plates include spikes projecting from said surfaces to penetrate the two spinous processes or laminae, whereby said plates may be fixated to the two spinous processes or laminae by application of a suitable compressive force.

51. A method of providing additional stabilization for a portion of a spine, wherein the spine is initially stabilized by a first pair of longitudinal plates such that a medial surface of each plate of the first pair of longitudinal plates is contacting two adjacent spinous processes or laminae on contralateral sides of a sagittal plane, wherein the first pair of longitudinal plates are connected by a first post extending through a first interspinous gap between the two adjacent spinous processes or laminae; and wherein each plate of the first pair of longitudinal plates includes a plate connection mechanism at a first end thereof allowing in-situ plate connection while accommodating a kyphotic or lordotic curvature of the spine;

the method comprising the steps of:
connecting an additional pair of longitudinal plates to the first pair of longitudinal plates, wherein the additional pair of longitudinal plates includes a proximal plate connection mechanism that is connectable to the plate connection mechanism of the first pair of longitudinal plates, wherein the step of connecting the additional pair of longitudinal plates is performed in-situ without removal of the first post from the first pair of longitudinal plates;

contacting, at a distal end of each plate of the additional pair of longitudinal plates, a medial surface of each plate of the additional pair of longitudinal plates with an additional spinous process or laminae; and connecting each plate of the additional pair of longitudinal plates within an additional interspinous gap with an additional post.

52. The method according to claim 51 wherein the medial surfaces of the each plate of the additional pair of longitudinal plates includes spikes projecting from the surface to penetrate the additional spinous processes or laminae, the method further comprising the step of applying a compressive force to the additional pair of longitudinal plates when connecting the additional pair of longitudinal plates with the additional post, such that the additional pair of longitudinal plates are fixated to the additional spinous processes or laminae by application the compressive force.

53. The method according to claim 51 wherein the step of contacting the medial surface of each plate of each pair of the additional pairs of plates with an additional spinous process or laminae includes the step of contacting the medial surface of each plate of each pair of the additional pairs of plates with the atlas.

54. The method according to claim 51 wherein the step of contacting the medial surface of each plate of each pair of the additional pairs of plates with an additional spinous process or laminae includes the step of contacting the medial surface of each plate of each pair of the additional pairs of plates with the sacrum.

55. The method according to claim 51 wherein the additional pair of longitudinal plates is a first additional pair of longitudinal plates, the additional post is a first additional post, the additional interspinous gap is a first additional interspinous gap, the proximal plate connection mechanism is a first proximal plate connection mechanism, and the adjacent spinous processes or laminae is a first additional spinous process or laminae, wherein each plate of the first additional pair of longitudinal plates includes a first distal plate connection mechanism allowing in-situ plate connection while accommodating a kyphotic or lordotic curvature of the spine;

the method further comprising the steps of:
connecting a second additional pair of longitudinal plates to the first additional pair of longitudinal plates, wherein each plate of the second additional pair of longitudinal plates includes a second proximal plate connection mechanism that is connectable to the first distal plate connection mechanism of the first additional pair of longitudinal plates, wherein the step of connecting the second additional pair of longitudinal plates is performed in-situ without removal of the first additional post from the first additional pair of longitudinal plates;

contacting, at a distal end of each plate of the second additional pair of longitudinal plates, a medial surface of each plate of the second additional pair of longitudinal plates with a second additional spinous process or laminae; and connecting each plate of the second additional pair of longitudinal plates within a second additional interspinous gap with a second additional post.

56. The method according to claim 51 wherein the additional pair of longitudinal plates is a first additional pair of longitudinal plates, the additional post is a first additional post, the additional interspinous gap is a first additional interspinous gap, the proximal plate connection mechanism is a first proximal plate connection mechanism, and the adjacent spinous processes or laminae is a first additional spinous process or laminae, wherein each plate of the first additional pair of longitudinal plates includes a second plate connection mechanism at a second end thereof allowing in-situ plate connection while accommodating a kyphotic or lordotic curvature of the spine;

the method further comprising the steps of:
connecting a second additional pair of longitudinal plates to the first pair of longitudinal plates, wherein each plate of the second additional pair of longitudinal plates includes a second proximal plate connection mechanism that is connectable to the second plate connection mechanism of the first pair of longitudinal plates, wherein the step of connecting the second additional pair of longitudinal plates is performed in-situ without removal of the first additional post from the first additional pair of longitudinal plates;

contacting, at a distal end of each plate of the second additional pair of longitudinal plates, a medial surface of each plate of the second additional pair of longitudinal plates with a second additional spinous process or laminae; and connecting each plate of the second additional pair of longitudinal plates within a second additional interspinous gap with a second additional post.

* * * * *